US006840928B2

United States Patent
Datta et al.

(10) Patent No.: US 6,840,928 B2
(45) Date of Patent: Jan. 11, 2005

(54) STRETCHABLE ABSORBENT ARTICLE HAVING ZONES OF DIFFERENTIAL STRETCH

(75) Inventors: Paul Joseph Datta, Appleton, WI (US); Gary Lee Travis, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 325 days.

(21) Appl. No.: 10/025,307

(22) Filed: Dec. 19, 2001

(65) Prior Publication Data

US 2002/0165516 A1 Nov. 7, 2002

Related U.S. Application Data

(60) Provisional application No. 60/272,548, filed on Mar. 1, 2001.

(51) Int. Cl.$^7$ .................................................. A61F 13/15
(52) U.S. Cl. .................................................. 604/385.22
(58) Field of Search ..................... 604/385.01, 385.101, 604/385.16, 385.22, 385.28

(56) References Cited

U.S. PATENT DOCUMENTS

| | | |
|---|---|---|
| 4,486,192 A | 12/1984 | Sigl |
| 4,655,760 A | 4/1987 | Morman et al. |
| 4,661,102 A | 4/1987 | Shikata et al. |
| 4,662,877 A | 5/1987 | Williams |
| 4,663,220 A | 5/1987 | Wisneski et al. |
| 4,673,402 A | 6/1987 | Weisman et al. |
| 4,695,278 A | 9/1987 | Lawson |
| 4,699,620 A | 10/1987 | Bernardin |
| 4,701,171 A | 10/1987 | Boland et al. |
| 4,701,174 A | 10/1987 | Johnson |
| 4,704,114 A | 11/1987 | Wilson et al. |
| 4,704,116 A | 11/1987 | Enloe |
| 4,710,187 A | 12/1987 | Boland et al. |
| 4,756,709 A | 7/1988 | Stevens |
| 4,777,073 A | 10/1988 | Sheth |
| 4,798,603 A | 1/1989 | Meyer et al. |
| 4,834,738 A | 5/1989 | Kielpikowski et al. |
| 4,872,871 A | 10/1989 | Proxmire et al. |

(List continued on next page.)

FOREIGN PATENT DOCUMENTS

| | | |
|---|---|---|
| EP | 0217032 | 2/1992 |
| EP | 0587792 | 1/1998 |
| EP | 0 677 284 B1 | 6/1999 |
| EP | 0804132 | 6/1999 |

(List continued on next page.)

OTHER PUBLICATIONS

Federal Test Method Standard (FTMS) No. 191A, Method 5514, "Water Resistance of Cloth; Low Range, Hydrostatic Pressure Method," Jul. 20, 1978, 3 pages.

American Society for Testing Materials (ASTM) Designation: D 882–95a, "Standard Test Method for Tensile Properties of Thin Plastic Sheeting," pp. 182–187, published Dec. 1995.

INDA Standard Test Method IST 70.4 (99), "Standard Test Method for Water Vapor Transmission Rate Through Non Woven and Plastic Film Using a Guard Film and Vapor Pressure Sensor," last revised 1999, 7 pages.

*Primary Examiner*—John J. Calvert
*Assistant Examiner*—M. Bogart
(74) *Attorney, Agent, or Firm*—David J. Arteman; Alyssa A. Dudkowski

(57) ABSTRACT

A disposable absorbent article is provided which includes a substantially liquid-impermeable, stretchable outer cover, a liquid permeable, stretchable top surface, and an absorbent body located between the outer cover and the top surface. The stretchable top surface can further include a first zone and a second zone. The stretchable outer cover can be configured to provide a first level of elongation when subjected to a tensile force of 100 gmf per inch (per 2.54 cm) of width according to the Material Elongation and Deformation Tensile Test set forth herein, while the first zone provides a second level of elongation that is less than the first level of elongation.

44 Claims, 8 Drawing Sheets

U.S. PATENT DOCUMENTS

| | | | | |
|---|---|---|---|---|
| 4,892,598 A | | 1/1990 | Stevens et al. | |
| 4,909,803 A | | 3/1990 | Aziz et al. | |
| 4,941,933 A | | 7/1990 | Korpman | |
| 4,949,668 A | | 8/1990 | Heindel et al. | |
| 4,965,122 A | | 10/1990 | Morman | |
| 4,983,109 A | | 1/1991 | Miller et al. | |
| 5,037,416 A | | 8/1991 | Allen et al. | |
| 5,114,781 A | | 5/1992 | Morman | |
| 5,116,662 A | | 5/1992 | Morman | |
| 5,176,668 A | | 1/1993 | Bernardin | |
| 5,176,672 A | | 1/1993 | Bruemmer et al. | |
| 5,192,606 A | | 3/1993 | Proxmire et al. | |
| 5,226,992 A | | 7/1993 | Morman | |
| 5,269,775 A | | 12/1993 | Freeland et al. | |
| 5,360,422 A | | 11/1994 | Brownlee et al. | |
| 5,399,219 A | | 3/1995 | Roessler et al. | |
| 5,472,518 A | | 12/1995 | Patnode et al. | |
| 5,486,166 A | | 1/1996 | Bishop et al. | |
| 5,490,846 A | | 2/1996 | Ellis et al. | |
| 5,496,295 A | | 3/1996 | Wilfong et al. | |
| 5,496,298 A | | 3/1996 | Kuepper et al. | |
| 5,509,915 A | | 4/1996 | Hanson et al. | |
| 5,527,303 A | * | 6/1996 | Milby et al. | 604/385.16 |
| 5,540,796 A | | 7/1996 | Fries | |
| 5,554,143 A | | 9/1996 | Roe et al. | |
| 5,554,145 A | | 9/1996 | Roe et al. | |
| 5,569,232 A | | 10/1996 | Roe et al. | |
| 5,575,782 A | | 11/1996 | Hasse et al. | |
| 5,575,783 A | * | 11/1996 | Clear et al. | 604/385.22 |
| 5,595,618 A | | 1/1997 | Fries et al. | |
| 5,611,791 A | | 3/1997 | Gorman et al. | |
| 5,624,422 A | | 4/1997 | Allen | |
| 5,624,424 A | | 4/1997 | Saisaka et al. | |
| 5,650,223 A | | 7/1997 | Weinberger et al. | |
| 5,728,219 A | | 3/1998 | Allen et al. | |
| 5,730,919 A | | 3/1998 | Wilfong et al. | |
| 5,746,732 A | * | 5/1998 | Olsson et al. | 604/385.28 |
| 5,807,368 A | | 9/1998 | Helmer | |
| 5,807,371 A | | 9/1998 | Toyoda et al. | |
| 5,824,004 A | | 10/1998 | Osborn, III et al. | |
| 5,846,232 A | | 12/1998 | Serbiak et al. | |
| 5,865,824 A | | 2/1999 | Chen et al. | |
| 5,883,028 A | | 3/1999 | Morman et al. | |
| 6,028,240 A | | 2/2000 | Wessel et al. | |
| 6,036,805 A | | 3/2000 | McNichols | |
| 6,049,023 A | | 4/2000 | Blenke et al. | |
| 6,096,017 A | | 8/2000 | Osborn, III | |
| 6,245,401 B1 | | 6/2001 | Ying et al. | |
| 6,264,641 B1 | | 7/2001 | Van Gompel et al. | |
| 6,264,864 B1 | | 7/2001 | Mackay | |
| 6,287,287 B1 | | 9/2001 | Elsberg | |
| 6,316,687 B1 | | 11/2001 | Davis et al. | |
| 6,436,083 B1 | * | 8/2002 | Mishima et al. | 604/385.24 |
| 6,461,344 B1 | * | 10/2002 | Widlund et al. | 604/390 |
| 6,552,245 B1 | * | 4/2003 | Roessler et al. | 604/367 |
| 6,582,413 B2 | * | 6/2003 | Krautkramer et al. | 604/385.16 |
| 6,616,648 B2 | * | 9/2003 | Hermansson et al. | 604/385.27 |
| 6,679,869 B1 | * | 1/2004 | Schlinz et al. | 604/385.22 |
| 2001/0016720 A1 | * | 8/2001 | Otsubo | 604/385.22 |
| 2002/0128617 A1 | * | 9/2002 | Roe et al. | 604/367 |
| 2002/0161348 A1 | * | 10/2002 | Mishima et al. | 604/385.22 |
| 2003/0045855 A1 | * | 3/2003 | Ono et al. | 604/387 |

FOREIGN PATENT DOCUMENTS

| | | |
|---|---|---|
| EP | 1 064 893 A2 | 1/2001 |
| WO | WO 95/16425 A2 | 6/1995 |
| WO | WO 96/22064 A1 | 7/1996 |
| WO | WO 98/52506 A1 | 11/1998 |
| WO | WO 99/33424 A1 | 7/1999 |
| WO | WO 99/33425 A1 | 7/1999 |
| WO | WO 00/30584 A1 | 6/2000 |
| WO | WO 00/38911 A1 | 7/2000 |
| WO | WO 00/38913 A1 | 7/2000 |
| WO | WO 01/43969 A1 | 6/2001 |
| WO | WO 01/82849 A1 | 11/2001 |
| WO | WO 01/82850 A1 | 11/2001 |
| WO | WO 01/82851 A1 | 11/2001 |
| WO | WO 01/82852 A1 | 11/2001 |

* cited by examiner

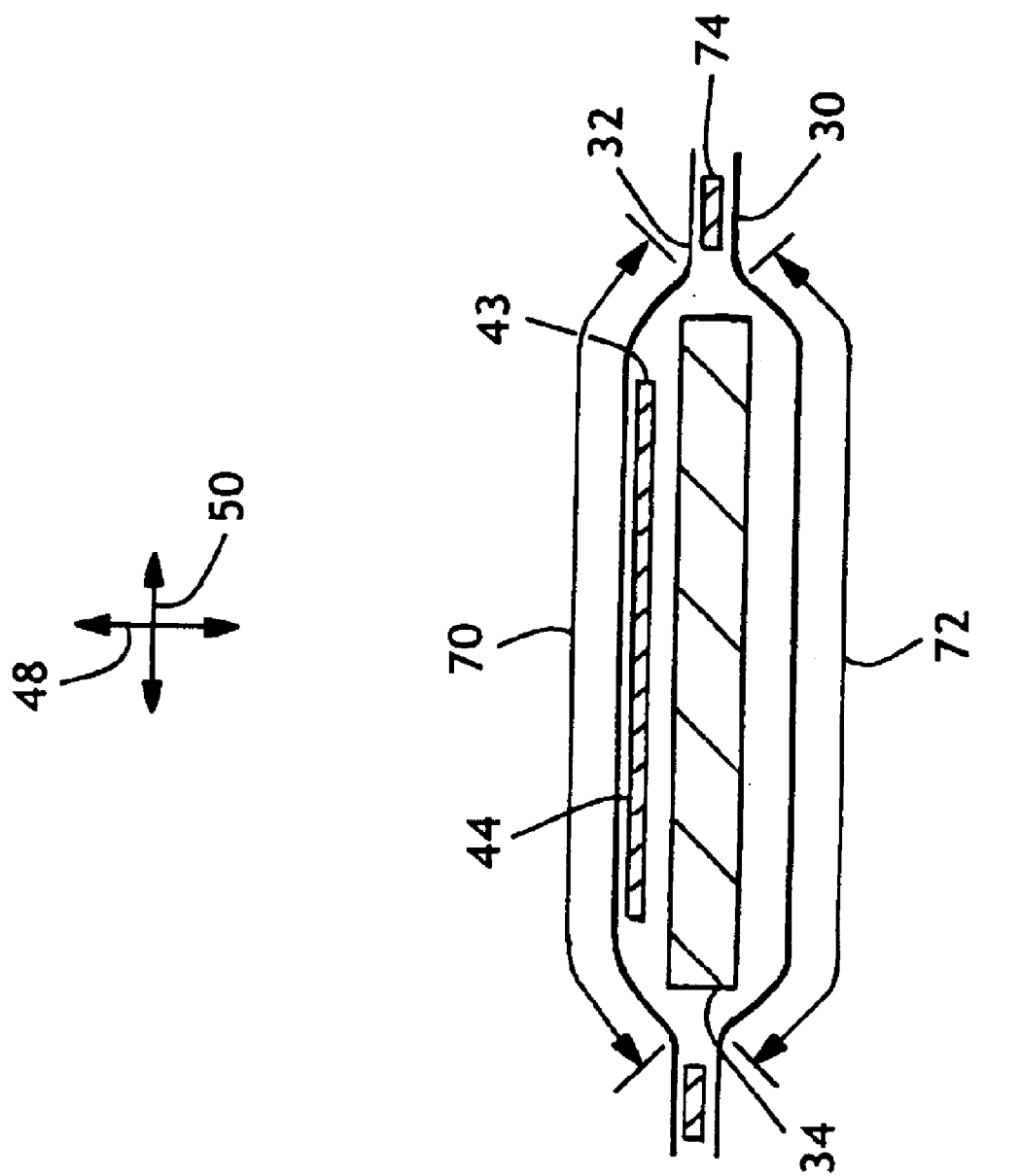

STRETCHABLE ABSORBENT ARTICLE HAVING ZONES OF DIFFERENTIAL STRETCH

This application is a non-provisional application of provisional application Ser. No. 60/272,548, filed on Mar. 1, 2001. The co-pending parent application is hereby incorporated by reference herein and is made a part hereof, including but not limited to those portions that specifically appear hereinafter.

BACKGROUND OF THE INVENTION

The present invention relates to stretchable absorbent articles, desirably disposable absorbent articles, which have a stretchable outer cover and distinctive stretchable top surface that has zones of differential stretch. Absorbent articles such as diapers, training pants or incontinence garments provide a close, comfortable fit about the wearer and contain body exudates when such articles perform properly. In certain circumstances, it can be desirable for absorbent articles to be capable of being pulled up or down over the hips of the wearer to allow the wearer or caregiver to easily pull the article on and easily remove the article if it has not been soiled. For example, such absorbent articles can assist in the toilet training of children.

Many conventional absorbent articles have typically employed fasteners that attach the waist sections of the articles around a wearer as well as various configurations of waist elastics, leg elastics, elasticized liners, and elasticized outer covers. The fasteners and elastic components have been employed to help produce and maintain the fit of the articles about the body contours of the wearer that can lead to improved containment. Maintaining this fit as the wearer moves and changes body position has been particularly difficult. For example, articles such as diapers are typically applied while the wearer is in a prone position such that their torso is extended and their abdomen is sunken. As the wearer changes from the prone position to a sitting position, the wearer's torso compresses and their abdomen extends outwardly thereby exerting forces on the article. If the waistband of the article does not have enough "give", such forces can cause the waistband to shift and can undesirably result in increased leakage.

In an attempt to provide a maintained fit during movement, some conventional absorbent articles have included an outer cover composed of elastomeric materials, such as elastomeric, stretch-bonded-laminate materials. Such materials have included a layer of meltblown elastomeric fibers that has been stretched and sandwiched between facing layers composed of polypropylene spunbond nonwoven materials. The meltblown layer has typically been pattern-bonded to the facing layers with thermal bonds, sonic bonds and/or adhesive bonds. Other conventional absorbent articles have included folded pleats in the outer cover. The pleats are arranged to expand open as the article absorbs liquids.

Moreover, in an attempt to improve the containment of exudates many absorbent articles incorporate containment components on the interior of the article. For example, the containment components may consist of containment flaps that are disposed toward the side edges of the article and extend generally in the longitudinal direction of the article. In addition, flaps or pockets may be included in the absorbent article to contain exudates from migrating in the lateral direction and leaking out of the article. Other absorbent articles have integrated the use of both longitudinal and lateral flaps on the interior surface of the product to further prevent the migration of exudates and improve the containment capabilities of the article.

However, many of such attempts to provide absorbent articles that provide the desired fit while maintaining containment have not been completely satisfactory. For example, absorbent articles having stretchable outer covers sometimes have not exhibited the desired resistance to leakage, as they have not readily expanded to provide void volume for the containment of fecal exudates. In addition, it has been found that in some instances, absorbent articles incorporating stretch characteristics can compromise components included in the article for containment purposes. As such, it is possible that the performance of the absorbent article can be impacted by the addition of stretchable materials, particularly in the area of containment. Specifically, in articles that combine stretchable components, such as a stretchable outer cover and an extensible bodyside liner, with containment components, the stretchable components may render the containment components less effective upon insult.

Specifically, when the absorbent core swells upon the intake of an insult, the stretchable bodyside liner may allow the absorbent to expand into the void volume that is to be created by the containment components, such as containment flaps. This difficulty can be enhanced in situations where the stretchable outer cover does not elongate as readily as the stretchable bodyside liner. Thus, when the absorbent body is allowed to expand into the area between the containment flaps, they become less effective, and possibly ineffective for containing subsequent insults or soiling.

Accordingly, despite the attempts to develop improved absorbent articles, there remains a need for absorbent articles that can provide improved fit and resistance to leakage without excessive irritation to the skin of the wearer. Moreover, in some circumstances, there remains a need that such absorbent articles provide the benefits of conventional training pants and conventional diapers. That is, there remains a need for stretchable absorbent articles that conform to the wearer for enhanced fit and comfort, and effectively maintain void volume for improved levels of containment.

BRIEF DESCRIPTION OF THE INVENTION

In response to the difficulties and problems discussed above, new absorbent article designs have been discovered that that are inherently more stretchable for improved fit and containment. Generally stated, the present invention provides a disposable absorbent article that defines a front waist section, a rear waist section, an intermediate section that extends between and connects the waist sections, a pair of laterally opposed side edges, a pair of longitudinally opposed waist edges, a longitudinal direction and a lateral direction. The absorbent article includes a substantially liquid-impermeable stretchable outer cover configured to provide a first level of elongation. The absorbent article also includes a liquid-permeable stretchable top surface attached to the stretchable outer cover. The stretchable top surface has a first zone (i.e. a particularized area) that is configured to provide a second level of elongation that is less than the first level of elongation found in the outer cover. The absorbent article also includes at least one containment component attached to the top surface and an absorbent body located between the outer cover and the top surface. As will be described in greater detail herein, the top surface includes the layer or layers between the wearer and the absorbent body that provide the bodyfacing surface of the article. For example, the top surface may include a bodyside liner with a surge management layer attached thereto.

In another aspect the present invention may provide a prefastened, pant-like disposable absorbent article that defines a front waist section, a rear waist section, an intermediate section that extends between and connects the waist sections, a pair of laterally opposed side edges, a pair of longitudinally opposed waist edges, a longitudinal direction and a lateral direction. The absorbent article includes a substantially liquid-impermeable stretchable outer cover configured to provide a first level of elongation. The absorbent article also includes a liquid-permeable stretchable top surface attached to the stretchable outer cover. The stretchable top surface has a first zone that is configured to provide a second level of elongation that is less than the first level of elongation found in the outer cover. The absorbent article also includes at least one containment component and an absorbent body located between the stretchable outer cover and the stretchable top surface. The absorbent article also includes a pair of fasteners refastenably attaching the laterally opposed side edges in the front waist section to the laterally opposed side edges in the rear waist section to provide a prefastened, pant-like absorbent article prior to packaging.

In yet another aspect, the present invention may provide a disposable absorbent article that defines a front waist section, a rear waist section, an intermediate section that extends between and connects the waist sections, a pair of laterally opposed side edges, a pair of longitudinally opposed waist edges, a longitudinal direction and a lateral direction. The absorbent article includes a substantially liquid-impermeable stretchable outer cover configured to provide a first level of elongation. The absorbent article also includes a liquid-permeable stretchable liner attached to the stretchable outer cover. The absorbent article further includes a pair of containment flaps attached to the stretchable bodyside liner. The absorbent article also includes a surge layer attached to the liquid permeable stretchable bodyside liner and an absorbent body located between the stretchable outer cover and the stretchable bodyside liner. The stretchable bodyside liner and the surge layer combine to provide a first zone that is configured to provide a second level of elongation that is less than the first level of elongation.

In other aspects the first zone of the stretchable top surface may be provided by the combination of a surge layer attached to an extensible bodyside liner; a tissue layer attached to an extensible bodyside liner; or a layer of adhesive applied to an extensible bodyside liner. The adhesive layer may be attached to the bodyside liner in a swirl pattern. In certain aspects, the first zone will at least partially overlap the absorbent body. As such, the first zone provides an area of differential stretch relative to the stretchable outer cover. Accordingly, this improves the containment function of the absorbent article by better maintaining the void volume provided by the article. That is, by stretching differentially, i.e. less, the first zone permits the containment components, such as containment flaps, to perform their function.

In yet other aspects, the outer cover may be extensible and configured to provide a first level of elongation of at least about 20 percent while the first zone of the top surface is configured to provide second level of elongation that is less than 20 percent. In particular, the first level of elongation is at least about 40 percent while the second level of elongation is less than 40 percent when subjected to a tensile force of 100 gmf per inch of width according to the Material Elongation and Deformation Tensile Test set forth herein.

In still other aspects, the stretchable top surface may define a second zone such that the second level elongation does not exceed the elongation of the second zone of the top surface. Therefore, the absorbent article may have areas of at least three elongations: the outer cover, the first zone of the top surface, and the second zone of the top surface. In addition, the stretchable outer cover may also be configured to provide a level of substantially permanent deformation of at least about 20 percent when subjected to the tensile force of 100 gmf per inch (per 2.54 cm) of width, while the first zone of the top surface is further configured to provide a level of substantially permanent deformation of less than 20 percent when subjected to the tensile force of 100 gmf per inch of width, and the second zone is configured to provide a substantially permanent deformation of at least about 20 percent when subjected to the tensile force of 100 gmf per inch (per 2.54 cm) of width.

In particular aspects, the stretchable top surface may be an extensible bodyside liner, and more specifically, a necked nonwoven web. The stretchable outer cover may include a necked laminate of at least one layer of a non-elastic, neckable material and at least one layer of a non-elastic film.

Absorbent articles of the present invention advantageously provide extensible absorbent articles that offer improved containment characteristics. In particular, the present invention includes absorbent articles having a stretchable outer cover and a stretchable top surface that provides reliable containment of bodily exudates, even upon repeated insults. Moreover, the absorbent articles of the present invention provide a stretchable absorbent article that offers improved maintenance of the void volume within the article, and enhances the effectiveness of the containment components of the article. In addition, the stretchability of the absorbent article of the present invention provides improved fit and comfort of the wearer. Accordingly, due to the improved fit of the article of the wearer, coupled with the enhanced containment capabilities provided, the likelihood of undesirable leakage is advantageously reduced.

It is understood that both the foregoing general description and the following detailed description are exemplary and are intended to provide further explanation of the invention claimed. The accompanying drawings, which are incorporated in and constitute part of this specification, are included to illustrate and provide a further understanding of the diaper of the present invention. Together with the description, the drawings serve to explain the various aspects of the invention.

BRIEF DESCRIPTION OF THE DRAWINGS

The present invention will be more fully understood and further advantages will become apparent when reference is made to the following detailed description of the invention and the drawings, in which:

FIG. 9 representatively shows a lateral cross-sectional view of an example of the absorbent article produced for use in connection with the Example described herein.

DETAILED DESCRIPTION OF THE INVENTION

Figure 1:
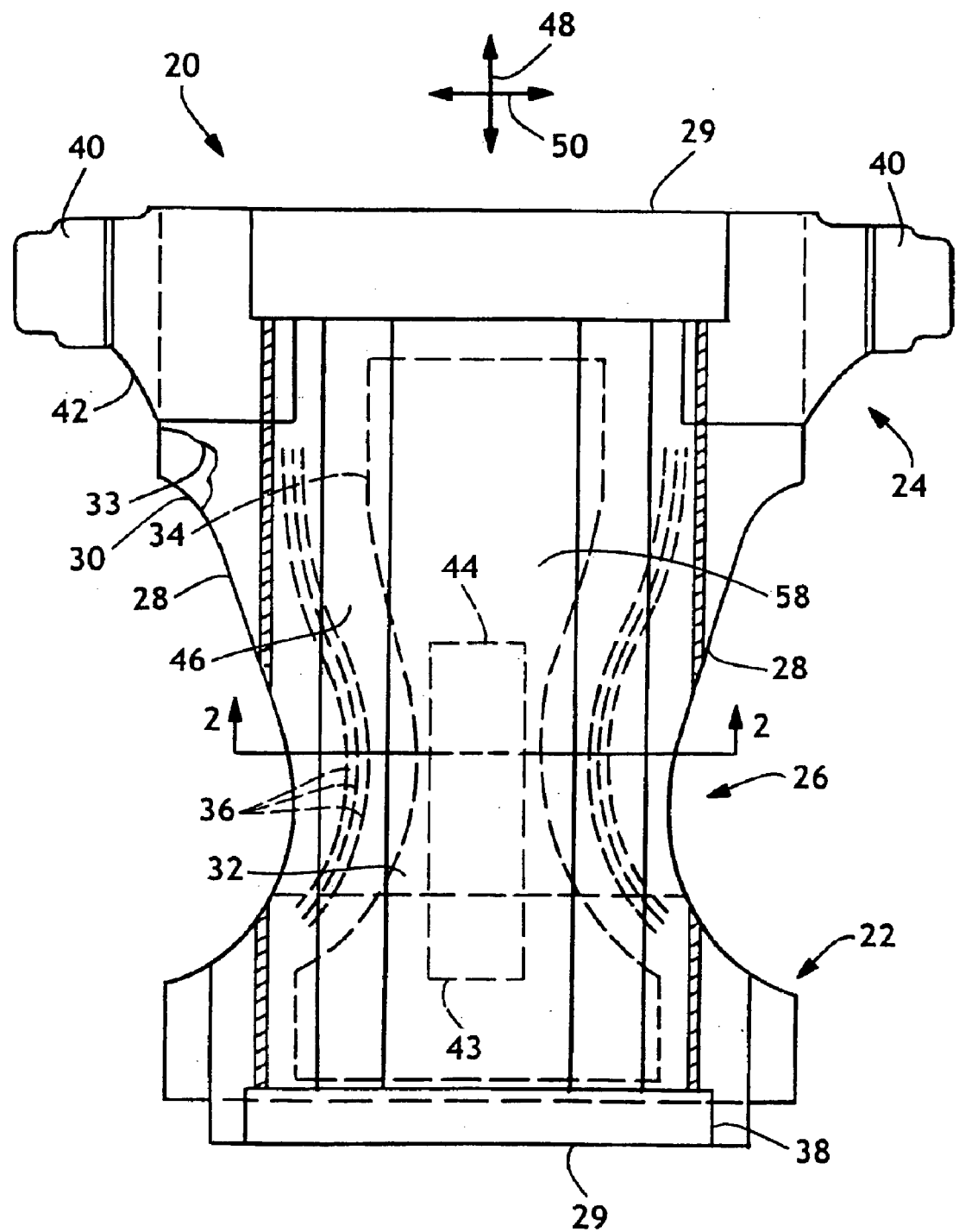
FIG. 1 representatively shows a top plan view of the partially cut away, inward surface of an example of an article of the invention.

The various aspects and embodiments of the invention will be described in the context of disposable absorbent articles, such as a disposable diaper or training pant. It is, however, readily apparent that the present invention could also be employed with other absorbent articles, such as feminine care articles, incontinence garments and the like. Typically, the disposable articles are intended for limited use and are not intended to be laundered or otherwise cleaned for reuse. A disposable diaper, for example, is discarded after it has become soiled by the wearer.

By incorporating its various aspects, the articles of the present invention can provide improved fit and improved containment of exudates. In particular, the stretchable outer cover of the articles is capable of adjusting to the wearer's movements and the wearer's body position and dimensions for improved performance. Further, absorbent articles of the present invention provide improved containment of bodily exudates by better maintaining the void volume of the article that includes stretchable components even after repeated insults. In addition, the articles of the invention can provide improved, greater softness, greater coverage over the hips and buttocks of the wearer and more cloth-like properties. Moreover, in certain aspects, the present invention can advantageously provide pant-like, prefastened, refastenable, absorbent articles that are capable of being reliably pulled up or down over the hips of the wearer to assist in the toilet training of the wearer similar to conventional training pants.

As used herein, the terms "attached" and "bonded" both refer to the joining, adhering, connecting, or the like, of two elements. Two elements will be considered to be bonded and/or attached together when they are bonded or attached directly to one another or indirectly to one another, such as when each is directly bonded or attached to intermediate elements.

When employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Accordingly, such terms are intended to be synonymous with the words "has", "have", "having", "includes", "including" and any derivatives of these words.

As used herein, the term "connected" refers to the joining, adhering, bonding, attaching, or the like, of two elements. Two elements will be considered to be connected together when they are connected directly to one another or indirectly to one another, such as when each is directly connected to intermediate elements.

As used herein, the term "elastic" or "elastomeric" refers to that property of a material where upon removal of an elongating force, the material is capable of substantially recovering its original size and shape or the material exhibits a significant retractive force.

As used herein, the term "extensible material" refers to that property of a material where upon removal of an elongating force, the material experiences a substantially permanent deformation or the material does not exhibit a significant retractive force.

As used herein, the term "hydrophilic" describes fibers or the surfaces of fibers, which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

As used herein, the term "layer" when used in the singular can have the dual meaning of a single element or a plurality of elements.

As used herein, the term "liquid impermeable" when used to describe a layer or laminate means that liquid such as urine will not pass through the layer or laminate under ordinary use conditions in a direction generally perpendicular to the plane of the layer or laminate at the point of liquid contact.

As used herein, the term "nonwoven web" means a web of material that is formed without the aid of a textile weaving or knitting process.

As used herein, the term "permanently bonded" refers to the joining, adhering, connecting, attaching, or the like, of two elements of an absorbent garment such that the elements tend to be and remain bonded during normal use conditions of the absorbent garment.

As used herein, the term "Releasably attached," "releasably bonded," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

As used herein, the term "surface" includes any layer, film, woven web or fabric, nonwoven web or fabric, laminate, composite, or the like, whether pervious or impervious to air, gas, and/or liquids.

As used herein, the term "stretchable" refers to a material that may be extensible and/or elastic. That is, the material may be extended, deformed or the like, without breaking, and may or may not significantly retract after removal of an extending force.

As used herein, the term "top surface" refers to the layer or layers that is on the bodyfacing side of the absorbent article and is configured to be disposed between the absorbent body and the wearer. That is, the top surface is the layer or layers of material that is configured to be located between the absorbent body and the body of the wearer. The top surface, or a layer included in the top surface, is ultimately intended to have substantial contact with the body of the wearer. As stated above, the top surface may consist of one layer or a plurality of layers. For example, the top surface may be a bodyside liner together with a surge layer attached the bodyside liner.

As used herein, the term "void volume" refers to a volume of space provided by an absorbent article and/or components of the absorbent article that is designed to receive and in some cases contain bodily exudates such as feces and/or urine. For example, void volume may be provided within the space created between the containment flaps, the top surface and the wearer during use.

The absorbent article of the present invention may be described as a diaper having a stretchable outer cover, a stretchable top surface, and an absorbent body located between the outer cover and the top surface. In particular, the stretchable top surface features first and second zones where the first zone of the top surface is less stretchable than the outer cover, and the second zone may advantageously have similar stretch capabilities as the outer cover. As such, when the absorbent body swells upon insult, the stretchable outer cover will be more apt to extend than the first zone of the stretchable top surface. Accordingly, the first zone ensures that the void volume provided by the absorbent article and its components are maintained, thus improving containment and reducing the likelihood of leakage.

Figure 2:
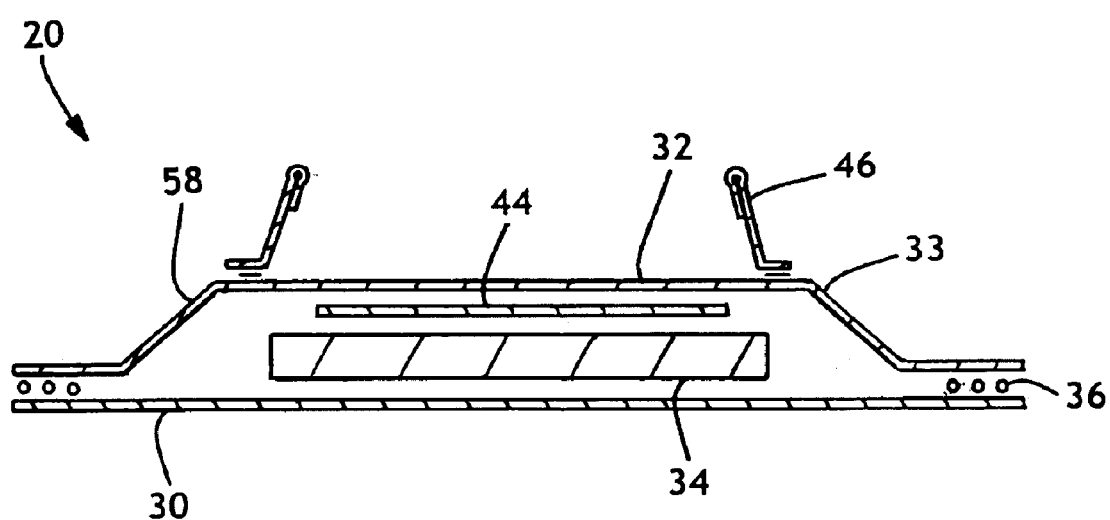
FIG. 2 representatively shows an expanded, lateral cross-sectional view taken with respect to line 2—2 of FIG. 1.
Figure 4:
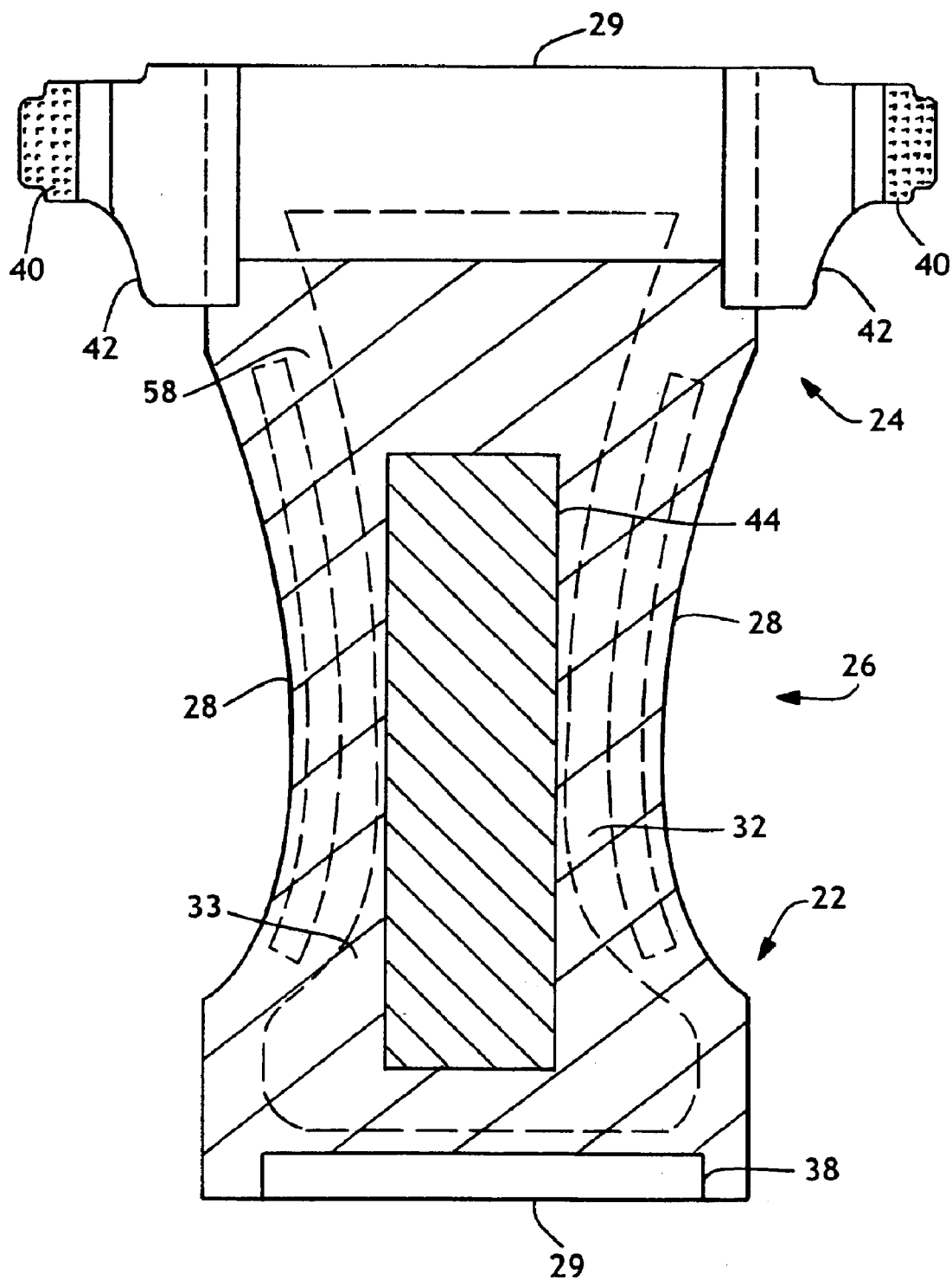
FIG. 4 representatively shows a top plan view of the inward surface of an example of an article of the present invention with some components removed for clarity where the first and second zones are emphasized with cross-hatching.
Figure 5:
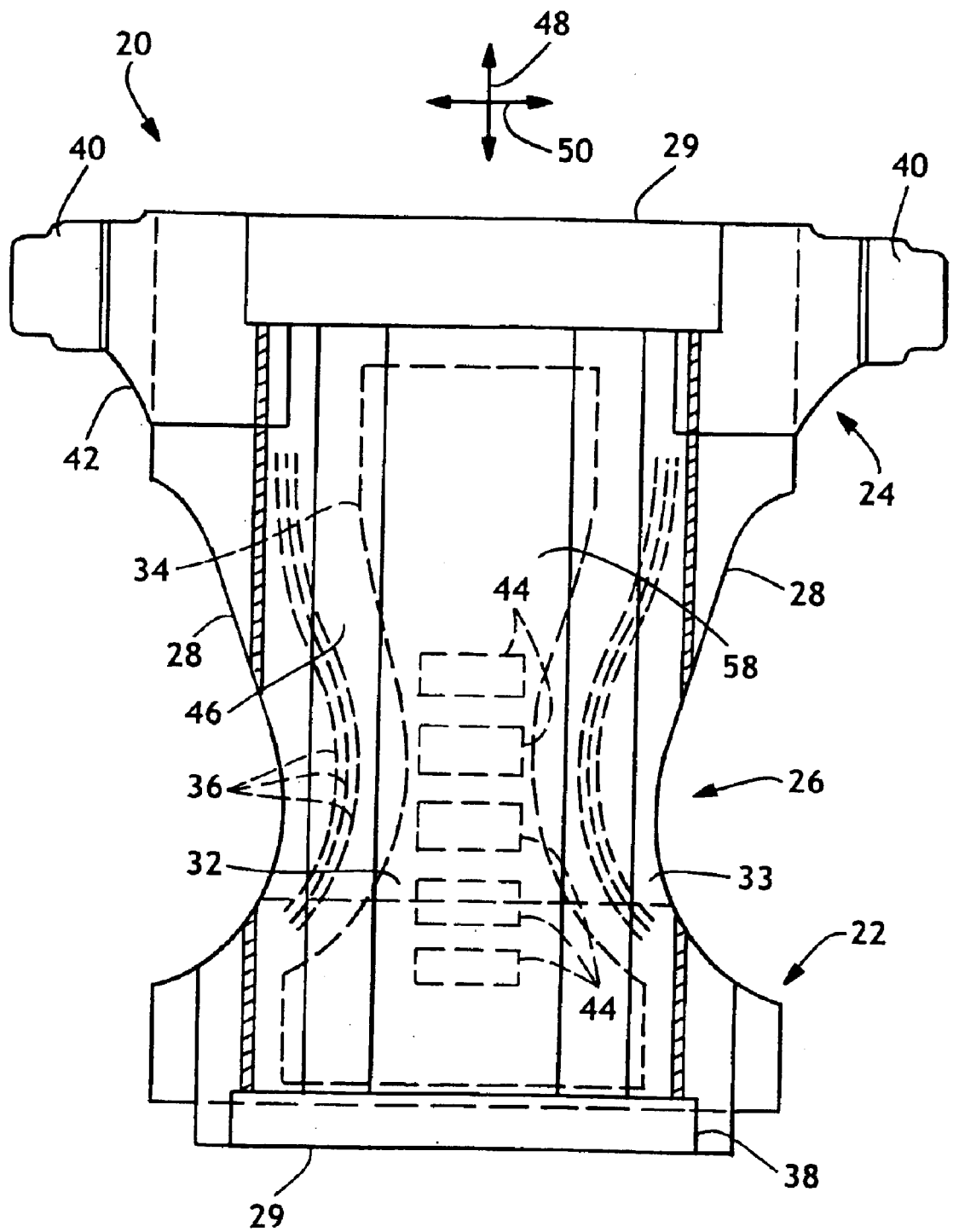
FIG. 5 representatively shows a top plan view of the inward surface of an article of the present invention featuring one alternative example of the configuration of the first zone.

Turning now to the Figures, FIG. 1 is a representative plan view of an absorbent article, such as disposable diaper 20, of the present invention in its flat-out, uncontracted state (i.e., with all elastic induced gathering and contraction removed). Portions of the bodyside liner 33 are partially cut away to more clearly show the surface of the diaper which contacts the wearer is facing the viewer. FIG. 2 representatively shows a sectional view of the absorbent article of FIG. 1 taken along line 2—2. With reference to FIGS. 1, 4 and 5, the disposable diaper 20 generally defines a front waist section 22, a rear waist section 24, and an intermediate section 26 which interconnects the front and rear waist sections. The diaper 20 also includes a pair of laterally opposed side edges 28 and a pair of longitudinally opposed waist edges 29. The front and rear waist sections 22 and 24 include the general portions of the article which are constructed to extend substantially over the wearer's front and rear abdominal regions, respectively, during use. The intermediate section 26 of the article includes the general portion of the article that is constructed to extend through the wearer's crotch region between the legs. Thus, the intermediate section 26 is an area where repeated liquid surges typically occur in the diaper or other disposable absorbent article.

The absorbent article includes an outer cover 30, a liquid permeable top surface 32 positioned in facing relation with the outer cover 30, and an absorbent body 34, such as an absorbent pad, which is located between the outer cover 30 and top surface 32. The outer cover 30 defines a length and a width which, in the illustrated embodiment, coincide with the length and width of the diaper 20. The absorbent body 34 generally defines a length and width that are less than the length and width of the outer cover 30, respectively. Thus, marginal portions of the diaper 20, such as marginal sections of the outer cover 30, may extend past the terminal edges of the absorbent body 34. In the illustrated embodiments, for example, the outer cover 30 extends outwardly beyond the terminal marginal edges of the absorbent body 34 to form side margins and end margins of the diaper 20. The top surface 32 is generally coextensive with the outer cover 30 but may optionally cover an area which is larger or smaller than the area of the outer cover 30, as desired. The outer cover 30 and top surface 32 are intended to face the garment and body of the wearer, respectively, while in use.

To provide improved fit and to help reduce leakage of body exudates from the diaper 20, the diaper side margins and end margins may be elasticized with suitable elastic members, such as single or multiple strands of elastic. For example, as representatively illustrated in FIGS. 1 and 2, the diaper 20 may include leg elastics 36 which are constructed to operably gather and shirr the side margins of the diaper 20 to provide elasticized leg bands which can closely fit around the legs of the wearer to reduce leakage and provide improved comfort and appearance. Similarly, waist elastics 38 can be employed to elasticize the end margins of the diaper 20 to provide elasticized waistbands. The waist elastics are configured to operably gather and shirr the end margins to provide a resilient, comfortably close fit around the waist of the wearer. In FIGS. 1, 4, and 5, the elastic members are illustrated in their uncontracted, stretched condition for the purpose of clarity.

Materials suitable for use as the leg elastics 36 and waist elastics 38 are well known to those skilled in the art. Exemplary of such materials are sheets or strands or ribbons of a polymeric, elastomeric material which are adhered to the outer cover 30 in a stretched position, or which are attached to the outer cover 30 while the outer cover is pleated, such that elastic constrictive forces are imparted to the outer cover 30. The leg elastics may also include such materials as polyurethane, synthetic and natural rubber that may optionally be heat shrinkable or heat elasticizable.

Fastening means, such as hook and loop fasteners 40, may be employed to secure the diaper on a wearer. Alternatively, other fastening means, such as buttons, pins, snaps, adhesive tape fasteners, cohesives, mushroom-and-loop fasteners, or the like, may be employed. The fasteners 40 can be located at either or both of the front and rear waist sections 22 and 24. For example, in the representatively shown embodiment, each of the hook fasteners 40 are assembled and attached to extend from the side panels 42 that are attached to the laterally opposed side edges in the rear waist section 24. Such fastening systems generally comprise a "hook" or hook-like, male component, and a cooperating "loop" or loop-like, female component which engages and releasably interconnects with the hook component. Desirably, the interconnection is selectively releasable and re-attachable.

Conventional hook and loop fastening systems are, for example, available under the VELCRO trademark. In a particular embodiment, the fasteners 40 may be a microhook material such as that distributed under the designation CS200 by 3M Company, a business having offices in St. Paul, Minn. Another suitable micro-hook material is distributed under the designation VELCRO CFM-29 1058, and is available from VELCRO U.S.A., Inc., a business having offices in Manchester, N.H.

The loop element may be provided directly by the outer cover 30 of the diaper 20 to provide a "fasten anywhere"

mechanical fastening system for improved fastening. Alternatively, as representatively illustrated in FIG. 3, the diaper 20 may include one or more attachment panels 66 to which the fasteners 40 are configured to releasably engage. For example, when the fasteners 40 are hook fasteners located in the rear waist section 24 of the diaper 20 as illustrated, the diaper may include a corresponding attachment panel 66 such as a complementary loop element on the outward facing surface in the front waist section 22. The attachment panels 66 may be provided by a woven fabric, a nonwoven fabric, a knitted fabric, a perforated or apertured layer, and the like, as well as combinations thereof. For example, a suitable material for the attachment panel can be composed of a 2 bar, warp knit fabric of the type available from Guilford Mills, Inc., Greensboro, N.C. under the trade designation #34285, as well other of knit fabrics.

In the illustrated embodiment, the diaper 20 further includes a pair of side panels 42 to which the fasteners 40 are attached. Generally, the side panels 42 are attached to the side edges of the diaper 20 in one of the waist sections and extend laterally outward therefrom. The side panels 42 may be elastic or otherwise rendered elastomeric.

For example, the side panels 42 may be an elastomeric material such as a neck-bonded laminate (NBL) or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., the disclosures of which are hereby incorporated by reference. Examples of articles that include elasticized side panels and selectively configured fastener tabs are described in U.S. Pat. No. 5,496,298 issued Mar. 5, 1996 to Kuepper et al.; U.S. Pat. No. 5,540,796 to Fries; and U.S. Pat. No. 5,595,618 to Fries; the disclosures of which are also incorporated herein by reference.

In the various configurations of the invention, the side panels 42 may be integrally formed with a selected diaper component. For example, the side panels 42 can be integrally formed from the layer of material that provides the outer cover 30, or may be integrally formed from the material employed to provide the top surface 32. In alternative configurations, the side panels 42 may be provided by one or more separately provided members that are connected and assembled to the outer cover 30, to the top surface 32, in between the outer cover and top surface, or in various fixedly attached combinations of such assemblies.

The diaper 20 may also include a surge management layer 43 located between the bodyside liner 33 and the absorbent body 34 to prevent pooling of the fluid exudates and further improve the distribution of the fluid exudates within the diaper 20. For example, as representatively illustrated in FIGS. 1–3 and 7 the surge management layer 43 is shown to be integrally attached to the bodyside liner 33, and as such combining with the bodyside liner 33 to provide the top surface 32, as will be discussed in greater detail below. Examples of suitable surge management layers are described in U.S. Pat. No. 5,486,166 to Bishop and U.S. Pat. No. 5,490,846 to Ellis, the entire disclosures of which are hereby incorporated by reference.

The diaper 20 may further include a ventilation layer (not illustrated) located between the absorbent body 34 and the outer cover 30 to insulate the outer cover 30 from the absorbent body 34 to reduce the dampness of the garment facing surface of the outer cover 30.

The disposable diaper 20 of the different embodiments of the present invention can also include containment components to reduce the possibility of leakage of bodily exudates from the diaper. For example, as representatively illustrated in FIGS. 1–3, 5 and 7, the diaper 20 may include a pair of containment flaps 46 that are configured to provide a barrier to the lateral flow of body exudates. The containment flaps 46 may be located along the laterally opposed side edges of the diaper 20 adjacent the side edges of the absorbent body 34. Each containment flap 46 typically defines an unattached edge which is configured to maintain an upright, perpendicular configuration in at least the intermediate section 26 of the diaper 20 to form a seal against the wearer's body. The containment flaps 46 may extend longitudinally along the entire length of the absorbent body 34 or may only extend partially along the length of the absorbent body 34. When the containment flaps 46 are shorter in length than the absorbent body 34, the containment flaps 46 can be selectively positioned anywhere along the side edges of the diaper 20 in the intermediate section 26. In a particular aspect of the invention, the containment flaps 46 extend along the entire length of the absorbent body 34 to better contain the body exudates.

Such containment flaps 46 are generally well known to those skilled in the art. For example, suitable constructions and arrangements for containment flaps 46 are described in U.S. Pat. No. 4,704,116 issued Nov. 3, 1987, to K. Enloe, the disclosure of which is hereby incorporated by reference.

Alternatively, the diaper 20 of the present invention may also incorporate other containment components in addition to or instead of containment flaps 46. Other containment components may include, but are not limited to, elasticized waist flaps, foam dams in the waist or crotch region, and the like.

The diaper 20 may be of various suitable shapes. For example, the diaper may have an overall rectangular shape, T-shape or an approximately hour-glass shape. In the shown embodiment, the diaper 20 has a generally I-shape. Examples of diaper configurations suitable for use in connection with the instant invention which may include other components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996 to Hanson et al., the disclosures of which are herein incorporated by reference.

The various components of the diaper 20 are integrally assembled together employing various types of suitable attachment means, such as adhesive, sonic bonds, thermal bonds or combinations thereof. In the shown embodiment, the top surface 32, in the form of a bodyside liner 33 with a surge layer 43 attached thereto, and outer cover 30 may be assembled to each other and to the absorbent body 34 with lines or other patterns of adhesive, such as a hot melt, pressure-sensitive adhesive. Similarly, other diaper components, such as the elastic members 36 and 38, and fastening members 40 may be assembled into the article by employing the above-identified attachment mechanisms.

The absorbent article of the different aspects of the present invention includes a distinctive stretchable outer cover 30 that may include a stretchable nonwoven layer which is operatively attached or otherwise joined to extend over a major portion of the outward surface of the article. In regions where the stretchable outer cover 30 is not affixed to non-extensible portions of the article or otherwise restricted from elongating, the stretchable outer cover 30 can be free to advantageously expand upon the application of a minimal tensile force. In desired aspects, the outer cover 30 can be stretchable along the longitudinal direction 48, lateral direction 50, or along a combination of both the lateral and longitudinal directions.

In particular, it is desirable that at least one of the portions of the stretchable outer cover 30 located in the waist sections 22 and 24 is capable of extending in the lateral direction 50 to provide improved fit of the article about the wearer, and improved coverage of the hips and buttocks of the wearer particularly in the rear waist section. In certain aspects, the stretchable outer cover may extend in the lateral and longitudinal directions 50 and 48, and also permanently deform in at least the lateral direction 50. For example, if the fasteners 40 and or side panels 42 are located along the side edges in the rear waist section 24 of the diaper 20, at least a portion of the outer cover 30 in the rear waist section 24 will desirably stretch to provide enhanced coverage over the buttocks of the wearer in use for improved containment and aesthetics. The enhanced buttock coverage is due to the permanent deformation of the outer cover 30 in the rear waist section 24 when lateral forces are exerted to fasten the diaper 20 about the wearer.

Moreover, it is also desirable that at least portions of the stretchable outer cover 30 located over the absorbent body 34 can extend during use for improved containment. For example as described in greater detail below, it is desirable that as the absorbent body 34 absorbs fluid exudates and expands outwardly, the stretchable outer cover 30 can readily elongate and extend in correspondence with the expansion of the absorbent body 34.

The stretchable outer cover 30 may also be selectively elasticized in certain regions by attaching elastomeric components to the stretchable outer cover 30 in such regions. For example, the stretchable outer cover 30 may be elasticized adjacent the leg openings by attaching the leg elastics 36 to the stretchable outer cover 30. Moreover, if desired, substantially non-stretchable regions can be created in the stretchable outer cover 30 by attaching such regions to a substantially non-stretchable component. For example, as described below, the diaper 20 may include an attachment panel 66 attached to the stretchable outer cover 30 in the front waist section 22 of the diaper 20. If the attachment panel is made of a non-stretchable material it will limit the stretchability of the outer cover 30 in the region it is attached. Generally, it is desirable that the majority of the stretchable outer cover 30 remain stretchable in use for improved performance.

The stretchable outer cover 30 of the present invention is desirably capable of providing a selected elongation when subjected to an applied tensile force. In particular, the stretchable outer cover 30 can provide an elongation of at least about 10 percent, desirably at least about 20 percent, more desirably at least about 30 percent and even more desirably at least about 40 percent when subjected to a tensile force of 100 gmf per inch (per 2.54 cm) of width of the test sample according to the Material Elongation and Deformation Tensile Test set forth herein. Elongation less than those above may not provide the desired expansion for the improved fastening, containment, and enhanced buttock coverage discussed herein. In other aspects, the stretchable outer cover 30 can be capable of providing an elongation of from about 10 percent to about 200 percent and desirably from about 30 percent to about 100 percent when subjected to a tensile force of 100 gmf per inch (per 2.54 cm) of width of the test sample according to the Material Elongation and Deformation Tensile Test set forth herein.

In particular aspects, the stretchable outer cover 30 of the present invention may be configured to be substantially extensible. That is, the stretchable outer cover 30 may also desirably be capable of providing a selected, sustained deformation when subjected to an applied tensile force and then allowed to relax for a selected time period after removing the applied tensile force. The measurement of the selected time period begins immediately after the removal of the tensile force. Desirably, the sustained deformation is a substantially permanent deformation. The selected elongation and sustained deformation can occur at least along the lateral direction 50 of the article. Optionally, the selected elongation and sustained deformation can occur along the longitudinal direction 48 of the article, or may occur along both the lateral direction and longitudinal direction of the article.

Specifically, the stretchable outer cover 30 can provide a substantially permanent deformation of at least about 10 percent, desirably at least 15 percent, particularly at least about 17 percent, more desirably at least about 20 percent, even more desirably at least about 25 percent and yet even more desirably at least about 30 percent when subjected to a tensile force of 100 gmf per inch (per 2.54 cm) of width of the test sample according to the Material Elongation and Deformation Tensile Test set forth herein. Substantially permanent deformations less than those set forth above may not provide the desired improved fit, containment, and enhanced buttock coverage. In still other aspects, the stretchable outer cover 30 can provide a substantially permanent deformation of from about 10 to about 100 percent and desirably from about 17 to about 80 percent when subjected to the tensile force of 100 gmf per inch (per 2.54 cm) of width of the test sample according to the Material Elongation and Deformation Tensile Test set forth herein.

In particular aspects, the stretchable outer cover 30 can provide a combination of elongation and substantially permanent deformation as set forth above for improved performance. Alternatively, the stretchable outer cover 30 may be substantially elastic. The stretchable outer cover 30 may be configured to provide a selected elongation as described above, and then by virtue of its elastic properties substantially recovers its original size and shape after removal of the force causing elongation. While an elastic outer cover is commonly understood to include those materials that rapidly exhibit substantial retraction upon the removal of an elongating force, it should be understood by this disclosure that the present invention also contemplates elastic outer covers that have slower recovery capabilities. For example, an elastic outer cover may exhibit substantial retraction upon the removal of an elongating force within seconds, minutes, or even hours. Alternatively, it is understood by those skilled in the art that suitable elastic materials exist that may exhibit retraction upon the removal of an elongating force over the course of days, weeks or even months. Desirably, an elastic material used as the stretchable outer cover 30 of the present invention would demonstrate generally rapid retraction upon the removal of an elongating force.

It should be noted that the elongation, extension or permanent deformation properties of the stretchable outer cover 30 are determined when the outer cover 30 is dry. Additionally, the percentage of elongation, extension or permanent deformation can be determined in accordance with the following formula:

$$100*(L-L_O)/(L_O);$$

where: L=either: (a) extended length for elongation or extension; or (b) post extended length for set or deformation, and $L_O$=initial length.

The extension of the stretchable outer cover 30 of the different aspects of the present invention is particularly important when the article is provided in a pant-like configuration such as a conventional training pant or prefastened diaper that can be pulled up or down over the hips of the wearer in use. For example, as representatively illustrated in FIG. 3, the diaper 20 may be provided in a prefastened pant-like configuration prior to packaging by releasably engaging the fasteners 40 with the opposite waist section during the manufacturing process. In such a configuration, the diaper 20 and, in particular, the waist sections 22 and 24 of the diaper 20 must be capable of extending such that the diaper 20 can be pulled on over the hips of the wearer. The use of the stretchable outer cover 30 as described herein can provide the necessary levels of extensibility to allow the diaper 20 to function in a prefastened configuration.

Figure 3:
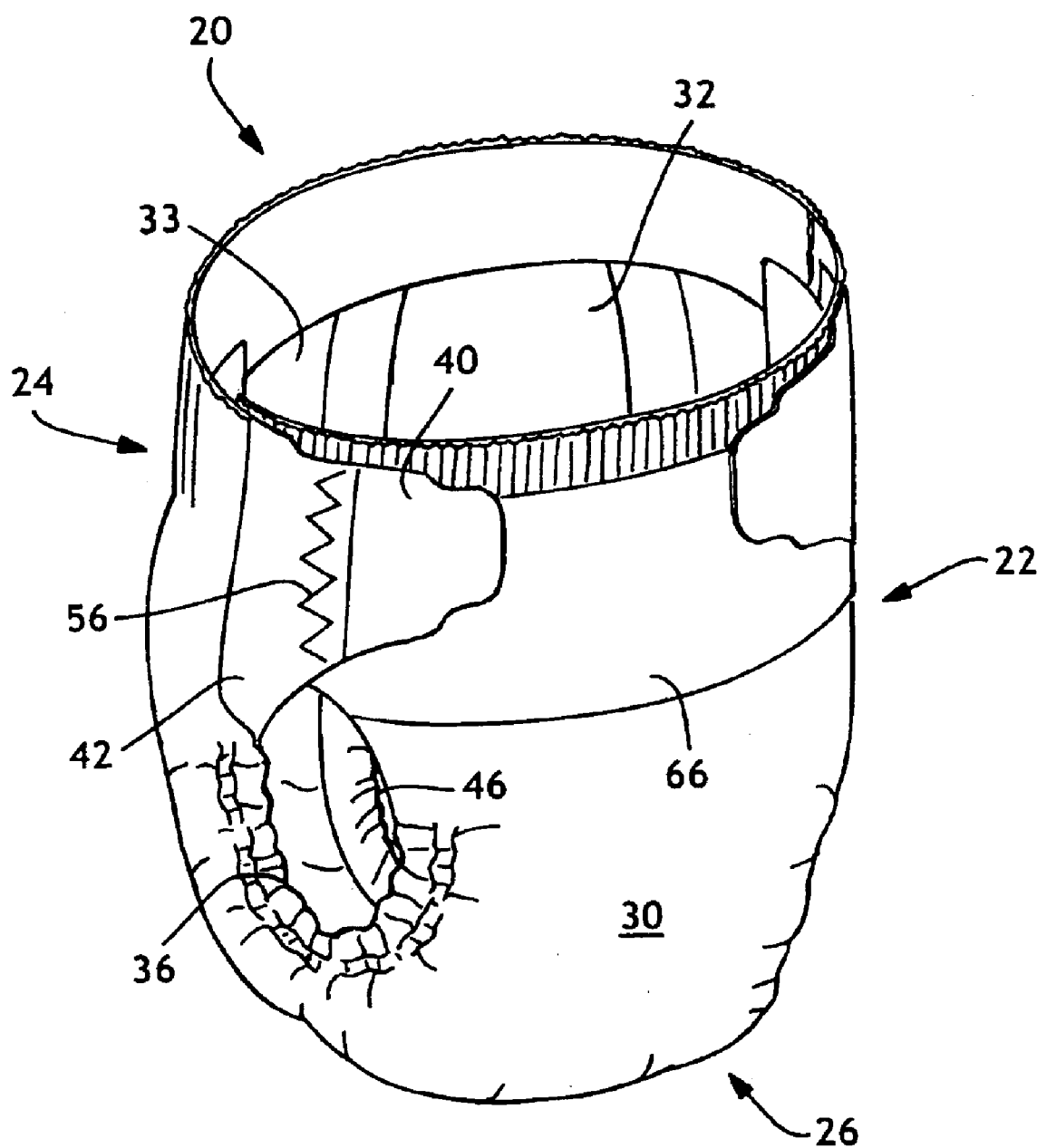
FIG. 3 representatively shows a perspective view of an example of an article of the invention in a prefastened, pant-like configuration.

As illustrated in FIG. 3, when in the pant-like configuration, the diaper 20 may include passive bonds 56 between the respective waist sections to assist the fasteners 40 in maintaining the diaper 20 in the prefastened configuration. Absorbent articles including such passive bonds and methods of making them are further described in U.S. Pat. No. 6,287,287 issued Sep. 11, 2001 to Elsberg, and U.S. Pat. No. 6,036,805 issued Mar. 14, 2000 to McNichols, the disclosures of which are hereby incorporated by reference.

In the various configurations of the invention, the stretchable outer cover 30 is also configured to be substantially impermeable to aqueous liquid. For example, the outer cover 30 can have a construction that is capable of supporting a selected hydrohead of water substantially without leakage therethrough. A suitable technique for determining the resistance of a material to liquid penetration is Federal Test Method Standard FTMS 191 Method 5514, 1978, or an equivalent thereof. Since the outer cover 30 is extensible, a layer of nylon net material having a thickness of about 0.1 mm may be needed to support the outer cover material for this test. The net material may be provided by nylon threads arranged in a hexagonal or honeycomb-like pattern with openings approximately 4 mm across. For example, the net material may be purchased from Wal-Mart Stores under the trade designation T-246. The net material is liquid pervious and does not significantly affect the hydrohead values obtained.

The stretchable outer cover 30 is sufficiently impermeable to liquid and semi-liquid materials to substantially prevent the undesired leakage of waste materials, such as urine and feces. For example, the stretchable outer cover 30 can desirably support a hydrohead of at least about 45 centimeters (cm) substantially without leakage. The stretchable outer cover 30 can alternatively support a hydrohead of at least about 55 cm, and optionally, can support a hydrohead of at least about 60 cm, or more, to provide improved benefits.

The stretchable outer cover 30 can be composed of various materials that can provide the desired properties set forth herein. For example, the stretchable outer cover 30 can be composed of a necked fabric, a creped fabric, a crimped fiber fabric, an extendable fiber fabric, a bonded-carded fabric, a micro-pleated fabric, polymer films or the like, as well as combinations thereof. The fabrics may be woven or nonwoven materials, such as spunbond fabrics. In a particular embodiment, the stretchable outer cover 30 can be composed of an extensible laminate of two or more layers. For example, the stretchable outer cover 30 may be a necked laminate formed from at least one neckable fabric laminated to at least one extendable film material wherein the necked laminate is extensible in at least one direction. The stretchable outer cover 30 may otherwise be a laminate formed from at least one necked fabric laminated to at least one extendable film material. In such a configuration, the laminate need not be necked. For the purposes of the present description, the term "nonwoven web" means a web of fibrous material that is formed without the aid of a textile weaving or knitting process. The term "fabrics" is used to refer to all of the woven, knitted and nonwoven fibrous webs.

As used herein, the term "neck" or "neck stretch" interchangeably means that the fabric is drawn such that it is extended under conditions reducing its width or its transverse dimension by drawing and elongating to increase the length of the fabric. The controlled drawing may take place under cool temperatures, room temperature or greater temperatures and is limited to an increase in overall dimension, in the direction being drawn, which does not exceed the elongation required to break the fabric. The necking process typically involves unwinding a sheet from a supply roll and passing it through a brake nip roll assembly driven at a given linear speed. A take-up roll or nip, operating at a linear speed higher than the brake nip roll, draws the fabric and generates the tension needed to elongate and neck the fabric. U.S. Pat. No. 4,965,122 entitled REVERSIBLY NECKED MATERIAL, by M. T. Morman which issued Oct. 23, 1990, the entire disclosure of which is hereby incorporated by reference, discloses a process for providing a reversibly necked nonwoven material which may include necking the material, then heating the necked material, followed by cooling.

As used herein, the term "neckable material or layer" means any material which can be necked such as a nonwoven, woven, or knitted material. As used herein, the term "necked material" refers to any material which has been drawn in at least one dimension, (e.g. lengthwise), reducing the transverse dimension, (e.g. width), such that when the drawing force is removed, the material can be pulled back to its original width. The necked material typically has a higher basis weight per unit area than the un-necked material. When the necked material is pulled back to its original un-necked width, the resultant material should have about the same basis weight as the un-necked material. This differs from stretching/orienting a material layer, during which the layer is thinned and the basis weight is permanently reduced.

Typically, such necked nonwoven fabric materials are capable of being necked up to about 80 percent. For example, the stretchable outer cover 30 of the various aspects of the present invention may be provided by a material that has been necked from about 10 to about 80 percent, desirably from about 20 to about 60 percent, and more desirably from about 30 to about 50 percent for improved performance. For the purposes of the present disclosure, the term "percent necked" or "percent neckdown" refers to a ratio or percentage determined by measuring the difference between the pre-necked dimension and the necked dimension of a neckable material, and then dividing that difference by the pre-necked dimension of the neckable material and multiplying by 100 for percentage. The percentage of necking (percent neck) can be determined in accordance with the description in the above-mentioned U.S. Pat. No. 4,965,122.

In a particular embodiment, the stretchable outer cover 30 can be made from a necked laminate material to provide the desired levels of stretchability as well as liquid impermeability and vapor permeability. For example, the stretchable outer cover 30 may be a necked laminate formed from sheet layers of at least one neckable fabric laminated to at least one film material wherein the necked laminate is extensible in at least one direction and does not appreciably retract. When the stretchable outer cover 30 is configured to be extensible, both the neckable fabric and the film material are non-elastic (but extensible) materials for increased permanent set, reduced cost and improved manufacturing efficiency.

By the term "non-elastic", what is meant is that the sheet layers are made from polymers that are generally considered to be inelastic. In other words, use of such inelastic polymers to form the sheet layers would result in sheet layers that are not elastic. As used herein, the term "elastic" means any material which, upon application of a biasing force, is stretchable, that is, elongatable, at least about 60 percent (i.e., to a stretched, biased length which is at least about 160 percent of its relaxed unbiased length), and which will immediately recover at least 55 percent of its elongation upon release of the stretching, elongating force, and over time recovers substantially all of its elongation.

Suitable necked laminates that include at least one nonelastic neckable material laminated to at least one nonelastic film material are described in U.S. patent application Ser. No. 09/455,513 filed Dec. 6, 1999 and entitled "TRANSVERSELY EXTENSIBLE AND RETRACTABLE NECKED LAMINATE OF NON-ELASTIC SHEET LAYERS", the entire disclosure of which is hereby incorporated by reference.

In such a configuration, the non-elastic film layer can be made from either cast or blown film equipment, can be coextruded and can be embossed if so desired. The film layer may be made from any suitable non-elastic polymer composition and may include multiple layers. The non-elastic film layer can also be breathable. For example, the non-elastic film layer may contain such fillers as micropore developing fillers, e.g. calcium carbonate; opacifying agents, e.g. titanium dioxide; and antiblock additives, e.g. diatomaceous earth. Suitable polymers for the non-elastic film layer include but are not limited to non-elastic extrudable polymers such as polyolefin or a blend of polyolefins, nylon, polyester and ethylene vinyl alcohol. More particularly, useful polyolefins include polypropylene and polyethylene. Other useful polymers include those described in U.S. Pat. No. 4,777,073 to Sheth, assigned to Exxon Chemical Patents Inc., such as a copolymer of polypropylene and low density polyethylene or linear low density polyethylene.

Alternative polymers for the film layer include those referred to as single site catalyzed polymers such as "metallocene" polymers produced according to a metallocene process and which have limited elastic properties. The term "metallocene-catalyzed polymers" as used herein includes those polymer materials that are produced by the polymerization of at least ethylene using metallocenes or constrained geometry catalysts, a class of organometallic complexes, as catalysts. For example, a common metallocene is ferrocene, a complex of a metal between two cyclopentadienyl (Cp) ligands. Such metallocene polymers are available from Exxon Chemical Company of Baytown, Tex. under the trade name EXXPOL for polypropylene based polymers, and EXACT for polyethylene based polymers; and from Dow Chemical Company of Midland, Mich. under the name ENGAGE. Preferably, the metallocene polymers are selected from copolymers of ethylene and 1-butene, copolymers of ethylene and 1-hexene, copolymers of ethylene and 1-octene and combinations thereof.

Suitable non-elastic neckable materials for such a configuration include nonwoven webs, woven materials and knitted materials such as those described in the abovementioned U.S. Pat. No. 4,965,122. Nonwoven fabrics or webs have been formed from many processes, for example, bonded carded web processes, meltblowing processes and spunbonding processes. The non-elastic neckable material is preferably formed from at least one member selected from fibers and filaments of inelastic polymers. Such polymers include polyesters, for example, polyethylene terephthalate, polyolefins, for example, polyethylene and polypropylene, polyamides, for example, nylon 6 and nylon 66. These fibers or filaments are used alone or in a mixture of two or more thereof. Suitable fibers for forming the neckable material include natural and synthetic fibers as well as bicomponent, multi-component, and shaped polymer fibers. Many polyolefins are available for fiber production according to the present invention, for example, fiber forming polypropylenes include Exxon Chemical Company's ESCORENE PD 3445 polypropylene and Himont Chemical Company's PF-304. Polyethylenes such as Dow Chemical's ASPUN 6811A linear low density polyethylene (LLDPE), 2553 LLDPE and 25355 and 12350 high density polyethylene are also suitable polymers.

The nonwoven web layer may be bonded to impart a discrete bond pattern with a prescribed bond surface area. If too much bond area is present on the neckable material, it can break before it necks. If there is not enough bond area, then the neckable material can pull apart. Typically, the percent bonding area useful in the present invention ranges from around 5 percent to around 40 percent of the area of the neckable material.

The non-elastic film layer may be laminated to the neckable material to form the laminate by conventional methods known in the art including adhesive bonding, point bonding, thermal point bonding, and sonic welding or the like, as well as combinations thereof. The laminate is then necked by conventional necking processes that typically vary the surface speed of the web to draw or neck the laminate. Such necking provides striated rugosities in the film and/or laminate resulting in transverse extensibility and retractability to the necked laminate and more "cloth-like" aesthetics. It is known that stretching and orienting a filled film layer causes micropores to form in the film, but longitudinal striated rugosities do not typically form in the film layer when stretched. The film layer would instead become physically thinner and may narrow slightly. By necking the laminate, the non-elastic neckable material, which is attached to the non-elastic film layer, can neck and bring the non-elastic film layer with it, thereby forming the longitudinal striated rugosities in the film which allow the film layer to become extendable in the transverse direction.

Alternative necked laminate materials that could be used to provide the outer cover 30 of the different aspects of the present invention are described in U.S. patent application Ser. No. 09/460,490 filed Dec. 14, 1999 and entitled "BREATHABLE LAMINATE PERMANENTLY CONFORMABLE TO THE CONTOURS OF A WEARER", the entire disclosure of which is hereby incorporated by reference.

Alternatively, in configurations where the stretchable outer cover 30 is configured to be substantially elastic, suitable materials may include multi-directional stretchable materials. One example of a suitable outer cover material is a 0.3 osy polypropylene spunbond that is necked 60% in the transverse direction 49 and creped 60% in the longitudinal direction 48, laminated with 3 grams per square meter (gsm) Findley 2525A styrene-isoprene-styrene based adhesive to 8 gsm PEBAX 2533 film with 20% $TiO_2$ concentrate. Other examples of suitable elastic materials suitable for the stretchable outercover 30 of the present invention are described in greater detail in U.S. Pat. No. 5,114,781 issued May 19, 1992 to Morman, and in U.S. Pat. No. 5,116,662 issued May 26, 1992 to Morman, and in U.S. Pat. No. 5,883,028 issued Mar. 16, 1999 to Morman et al. the disclosures of which are hereby incorporated by reference.

The absorbent article of the present invention also includes a distinctive stretchable top surface 32. The top surface 32, as representatively illustrated in FIGS. 1–5 and 7, presents a body-facing surface that is compliant, soft-feeling, and non-irritating to the wearer's skin.

For example, the top surface may be provided in part by a bodyside liner 33. In such embodiments where the top surface 32 is provided by a bodyside liner 33, the bodyside liner 33 can be less hydrophilic than absorbent body 34, and is sufficiently porous to be liquid permeable, permitting liquid to readily penetrate through its thickness to reach the absorbent composite. A suitable bodyside liner 33 may be manufactured from a wide selection of web materials, such as porous foams, reticulated foams, apertured plastic films, natural fibers (for example, wood or cotton fibers), synthetic fibers (for example, polyester or polypropylene fibers), or combinations of the above. The bodyside liner 33 is typically employed to help isolate the wearer's skin from liquids held in the absorbent body 34.

Various woven and nonwoven fabrics can be used for the bodyside liner 33. For example, the bodyside liner may be composed of a meltblown or spunbonded web of the desired fibers, and may also be a bonded-carded-web. Layers of different materials that may have different fiber deniers can also be used. The various fabrics can be composed of natural fibers, synthetic fibers or combinations thereof. The bodyside liner 33 may be composed of a substantially hydrophobic material, and the hydrophobic material may optionally be treated with a surfactant or otherwise processed to impart a desired level of wettability and hydrophilicity. In a particular embodiment of the invention, the bodyside liner 33 may be provided in part by a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28 percent Triton X-102 surfactant. The surfactant can be applied by any conventional means, such as spraying, printing, brush coating or the like.

In particular embodiments where the bodyside liner 33 is providing the top surface 32, it is desirably stretchable such that it is capable of extending with the outer cover 30 to assist in providing the improved fastening, fit and containment discussed above. For example, the bodyside liner 33 can be composed of various extensible materials such as a necked fabric, a creped fabric, a micro-pleated fabric, perforated polymer films or the like, as well as combinations thereof. The fabrics may be woven or nonwoven materials, such as spunbond fabrics, that may be elastic or non-elastic. Examples of suitable manufacturing techniques and suitable necked nonwoven fabric materials for such an extensible bodyside liner 33 are described in U.S. Pat. No. 4,965,122 entitled REVERSIBLY NECKED MATERIAL, by M. T. Morman which issued Oct. 23, 1990.

In particular aspects, the stretchable bodyside liner 33 can provide a combination of elongation and substantially permanent deformation for improved performance. Alternatively, the stretchable bodyside liner 33 may be substantially elastic. That is, the bodyside liner 33 may be configured to provide a selected elongation, and then by virtue of its elastic properties substantially recovers its original size and shape after removal of the force causing elongation. While an elastic bodyside liner is commonly understood to include those materials that rapidly exhibit substantial retraction upon the removal of an elongating force, it should be understood by this disclosure that the present invention also contemplates elastic bodyside liners that have slower recovery capabilities. For example, an elastic bodyside liner may exhibit substantial retraction upon the removal of an elongating force within seconds, minutes, or even hours. Alternatively, it is understood by those skilled in the art that suitable elastic materials exist that may exhibit retraction upon the removal of an elongating force over the course of days, weeks or even months. Desirably, an elastic material used as the stretchable bodyside liner 33 of the present invention would demonstrate generally rapid retraction upon the removal of an elongating force.

For example, the bodyside liner 33 can be composed of various elastic materials such as synthetic fibers (for example, polyester or polypropylene fibers), a combination of synthetic and natural fibers (examples of natural fibers including cotton fibers), porous foams, reticulated foams, apertured plastic films, or the like. The stretchable, elastic bodyside liner 42 can suitably be composed of a neck-stretched, spunbond web with KRATON G strands, such as 0.4 osy (60% neck-stretched) polypropylene spunbond laminated to 0.4 osy strands of KRATON MM G2760 with 12 strands per inch, which is stretched then allowed to retract. Other examples of suitable biaxially elastic materials suitable for the stretchable outercover 30 of the present invention are described in U.S. patent application Ser. No. 09/698,517 entitled "BIAXIAL STRETCH GARMENT," filed in the name of Vukos et al. on Oct. 27, 2000, the entire disclosure of which is hereby incorporated by reference.

Desirably, when included in the top surface 32, the bodyside liner 33 can be made from non-elastic neckable materials for reduced cost and improved manufacturing efficiency. Suitable non-elastic neckable materials for such a configuration include nonwoven webs, woven materials and knitted materials. Such webs providing the bodyside liner 33 can include one or more fabric layers. Nonwoven fabrics or webs have been formed from many processes, for example, bonded carded web processes, meltblowing processes and spunbonding processes. The non-elastic neckable material is preferably formed from at least one member selected from fibers and filaments of inelastic polymers. Such polymers include polyesters, for example, polyethylene terephthalate, polyolefins, for example, polyethylene and polypropylene, polyamides, for example, nylon 6 and nylon 66. These fibers or filaments are used alone or in a mixture of two or more thereof. Suitable fibers for forming the neckable material include natural and synthetic fibers as well as bicomponent, multi-component, and shaped polymer fibers. Many polyolefins are available for fiber production according to the present invention, for example, fiber forming polypropylenes can include Exxon Chemical Company's ESCORENE PD 3445 polypropylene and Himont Chemical Company's PF-304. Polyethylenes such as Dow Chemical's ASPUN 6811A linear low density polyethylene, 2553 LLDPE and 25355 and 12350 high density polyethylene are also suitable polymers. The nonwoven web layer may be bonded to impart a discrete bond pattern with a prescribed bond surface area. If too much bond area is present on the neckable material, it can break before it necks. If there is not enough bond area, then the neckable material can pull apart. Typically, the percent bonding area useful in the present invention ranges from around 5 percent to around 40 percent of the area of the neckable material.

For example, a particularly suitable extensible material for providing the bodyside liner 33 is a necked spunbond web of polypropylene fibers having a basis weight of from about 5 to about 30 gsm. Such a web may be necked up to about 80 percent.

The neckable material may be necked to form the extensible bodyside liner 33 by conventional necking processes that typically vary the surface speed of the web to draw or neck the material. Such necking will allow the material to extend and retract in the transverse direction. As discussed above, such necked nonwoven fabric materials typically are capable of being necked up to about 80 percent. For example, the extensible bodyside liner 33 of the various aspects of the present invention may be necked from about 10 to about 80 percent, desirably from about 20 to about 60 percent, and more desirably from about 30 to about 50 percent for improved performance.

The bodyside liner 33 and outer cover 30 are connected or otherwise associated together in an operable manner. As used herein, the term "associated" encompasses configurations in which bodyside liner 33 is directly joined to the outer cover 30, for example by affixing the bodyside liner 33 directly to the outer cover 30, and configurations wherein the bodyside liner 33 is indirectly joined to the outer cover 30, for example by affixing the bodyside liner 33 to intermediate members that in turn are affixed to the outer cover 30. The bodyside liner 33 and the outer cover 30 can, for example, be joined to each other in at least a portion of the diaper periphery by attachment mechanisms (not shown) such as adhesive bonds, sonic bonds, thermal bonds, pinning, stitching or any other attachment techniques known in the art, as well as combinations thereof.

For example, a uniform continuous layer of adhesive, a patterned layer of adhesive, a sprayed pattern of adhesive or an array of separate lines, swirls or spots of construction bonds may be used to affix the bodyside liner 33 to the outer cover 30. It should be readily appreciated that the above-described attachment mechanisms may also be employed to suitably interconnect, assemble and/or affix together the various other component parts of the articles that are described herein.

The diaper 20 of the different aspects of the present invention also includes an absorbent body 34 that provides an absorbent structure for holding and storing absorbed liquids and other waste materials. For example, as representatively illustrated in FIGS. 1,2,4 and 5 the absorbent body may be provided by an absorbent pad composed of selected hydrophilic fibers and high-absorbency particles. The absorbent body 34 may also be extensible or elastic. The absorbent body 34 is positioned and sandwiched between the top surface 32 and outer cover 30 to form the diaper 20. The absorbent body 34 has a construction that is generally compressible, conformable, non-irritating to the wearer's skin, and capable of absorbing and retaining body exudates. It should be understood that, for purposes of this invention, the absorbent body may comprise a single, integral piece of material, or alternatively, may comprise a plurality of individual separate pieces of material which are operably assembled together.

Various types of wettable, hydrophilic fibrous material can be used to form the component parts of absorbent body 34. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material that has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent body 34 can comprise a matrix of hydrophilic fibers, such as a web of cellulosic fluff, mixed with particles of high-absorbency material. In particular arrangements, the absorbent body 34 may comprise a mixture of superabsorbent hydrogel-forming particles or fibers and synthetic polymer meltblown fibers, or a mixture of superabsorbent particles or fibers with a fibrous coform material comprising a blend of natural fibers and/or synthetic polymer fibers.

The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent body, with lower concentrations toward the bodyside of the absorbent body and relatively higher concentrations toward the garment-side of the absorbent body. Alternative distributions and methods of achieving such distributions are well known to this skilled in the art. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent composite include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Synthetic absorbent gelling materials typically are xerogels that form hydrogels when wetted. The term "hydrogel", however, has commonly been used to also refer to both the wetted and unwetted forms of the material.

As mentioned previously, the high-absorbency material used in the absorbent body 34 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent body 34. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and alternatively is within the range of about 550–750 gsm to provide desired performance.

Optionally, a substantially hydrophilic tissue wrapsheet (not shown) may be employed to help maintain the integrity of the fibrous structure of the absorbent body 34. The tissue wrapsheet is typically placed about the absorbent body over at least the two major facing surfaces thereof and composed of an absorbent cellulosic material, such as creped wadding or a high wet-strength tissue that may or may not be pleated. In one aspect of the invention, the tissue wrapsheet can be configured to provide a wicking layer which helps to rapidly distribute liquid over the mass of absorbent fibers comprising the absorbent body 34. The wrapsheet material on one side of the absorbent fibrous mass may be bonded to the wrapsheet located on the opposite side of the fibrous mass to effectively entrap the absorbent body 34.

The top surface 32 of the different embodiments of the present invention can also include first and second zones 44 and 58. In particular, the first zone 44 is configured to have stretchability characteristics that are different than the other stretchable components of the diaper 20. In particular, the first zone 44 of the top surface 32 is desirably less stretchable than the stretchable outer cover 30. As such, the first zone 44 will help ensure that the void volume of the diaper 20 is maintained upon insult. That is, when the absorbent body 34 receives and absorbs bodily exudates, it generally expands, as will be described in greater detail below. This expansion of the absorbent body 34 in certain instances may generate enough force to deform the extensible components of the diaper, particularly the outer cover 30 and stretchable top surface 32. Accordingly, after insult, or repeated insults, it is possible that the absorbent body 34 may expand and deform the stretchable top surface 32, thereby consuming any void volume between the wearer and the top surface 32 that may be created by other components of the diaper 20.

Figure 6:
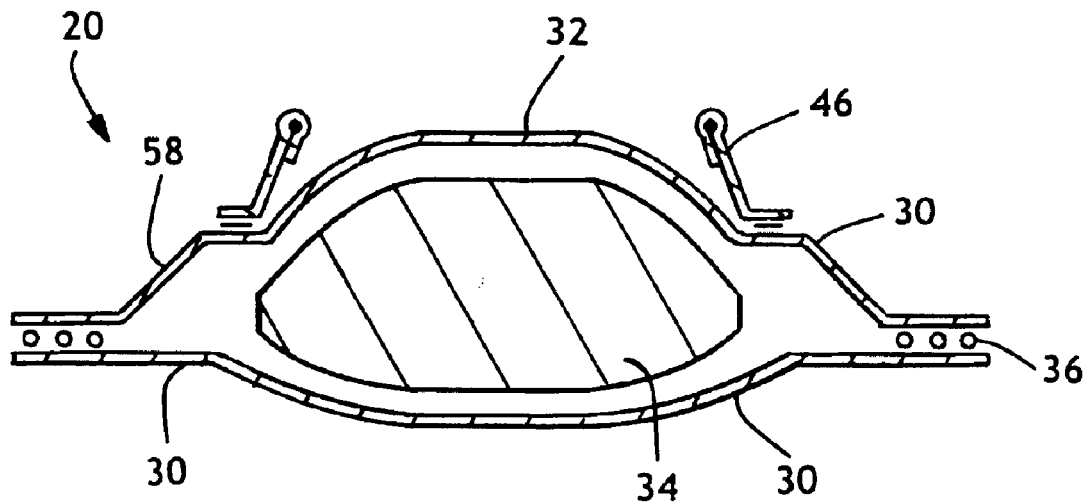
FIG. 6 representatively shows a lateral cross-sectional view of an example of an absorbent article having stretchable components but not having a first zone of differential stretch demonstrating how the void volume is consumed upon the swelling of the absorbent body during use of the article.
Figure 7:
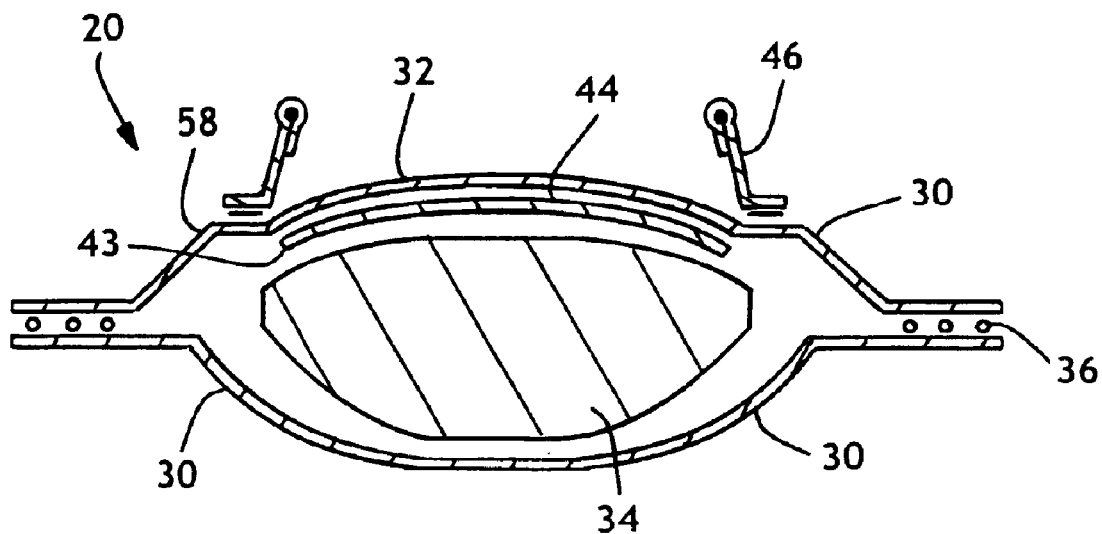
FIG. 7 representatively shows a lateral cross-sectional view of an example of an absorbent article of the present invention featuring a first zone, where the void volume is maintained upon the swelling of the absorbent body.

For example, as representatively illustrated in FIGS. 1–3, 5 and 7, the diaper 20 of the present invention may include containment flaps 46 extending longitudinally on the interior of the diaper 20. However, as representatively illustrated in FIG. 6, if the absorbent body 34 expands upon insult, it may expand enough to consume the void volume created by the containment flaps 46. In such a situation, bodily exudates contained within the void volume could pass over the top of the containment flap 46, thereby potentially, undesirably resulting in leakage out of the diaper. Likewise, the diaper could be more prone to possible leakage of future insults as well. In addition, other containment components such as the leg and waist elastics 36 and 29 may also be negatively impacted by the expansion of the absorbent body 34 into the void volume of the diaper 20. For example, the consumption of the void volume by the absorbent body 34 may excessively remove components such as leg elastics 36 and waist elastics 29 from close contact with the body of the wearer, further negatively impacting the fit and containment properties of the diaper 20.

Accordingly, if the first zone 44 was configured to be less stretchable than the outer cover 30 of the diaper 20, then the void volume provided by the containment components of the diaper would be better maintained. That is, as representatively illustrated in FIG. 7, with the expansion of the absorbent body 34 upon insult, the outer cover 30 of the diaper 20 of the present invention will extend and deform before portions of the top surface 32 extend and deform. This is due to the first zone 44 of the top surface 32 being more resistant to deformation than the stretchable outer cover 30. As such, void volume is maintained, thereby improving the containment characteristics of the diaper and reducing the possibility of leakage.

The reduction of stretchability of the top surface 32 in the first zone 44 can occur in at least the lateral direction 50 of the diaper 20. Optionally, the reduction of stretchability of the top surface 32 in the first zone 44 occurs in the longitudinal direction 48. Desirably, the selected reduction of stretch of the top surface 32 in the first zone 44 may occur in both the longitudinal 48 and the lateral 50 directions.

The first zone 44 may be of various shapes as are well known to those skilled in the art. For example, the first zone 44 may be round, square, elliptical, or triangular. In the illustrated embodiments, the first zone 44 is substantially rectangular in shape. Moreover, the first zone 44 may be a continuous body as shown in the illustrated embodiments.

Alternatively, the first zone 44 may be a plurality of discontinuous bodies of various shapes as described above, having similar extensibility characteristics less than those of the outer cover 30. For example, as representatively illustrated in FIG. 5, the first zone 44 may be a series of separate rectangles extending in the lateral direction located generally in the center of the diaper 20.

The total surface area of the first zone 44 may be any size relative to the size of the diaper 20. In a particular aspect the area of the first zone 44 would substantially encompass the intermediate section 26 of the diaper 20. Desirably, in the illustrated embodiment, the first zone 44 would extend substantially over the entire distance in the lateral direction 50 between the containment flaps 46. Alternatively, there may be some area in the intermediate section 26 between the containment flaps 46 that is not part of the first zone 44. Advantageously, the length in the lateral direction 50 in the intermediate section 26 between the containment flaps 46 that is not part of the first zone 44 is less than two inches. If this length becomes greater than two inches, the possibility of the top surface 32 being extended into the void volume created by the containment flaps 46 upon insult of the diaper 20 increases.

The first zone 44 may be located in any area of the top surface 32 in order to have some positive effects in maintaining the void volume of the diaper 20. Desirably, the first zone 44 is configured to be located in the intermediate section 26 of the diaper 20 between the containment flaps 46, in at least a partially overlapping relationship with the absorbent body 34. In such a configuration, the first zone 44 can be most effective in preserving the void volume of the diaper 20 after insult by restraining the extensibility of the top surface 32 over the absorbent body 34, thereby increasing the likelihood that the absorbent body 34 will instead extend the outer cover 30. For example, as representatively illustrated in FIG. 1, the entirety of the first zone 44 is located over the absorbent body 34 and between the containment flaps 46, thus being in a complete or 100% overlapping relationship with the absorbent body 34.

The top surface 32 of the different aspects of the present invention may also define a second zone 58. In particular, the second zone 58 is composed generally of that portion of the top surface 32 other than the portion that is the first zone 44. For example, as representatively illustrated in FIG. 4, the second zone 58 of the top surface 32 is provided by that portion of the bodyside liner 33 that surrounds the first zone 44. Accordingly, the second zone 58 generally surrounds the first zone 44, located substantially centrally in the top surface 32 of the diaper 20.

As such, the characteristics of the second zone 58 are defined by the material that provides the top surface 32, other than the first zone 44. The second zone 58 accordingly would generally be more stretchable than the first zone 44. Therefore, the first zone 44 is less stretchable than the second zone as well as the outer cover 30. As such, the top surface 32 retains advantageous stretchability characteristics in the second zone 58, thereby providing the wearer the benefit of improved fit and comfort, while the localized first zone 44 helps preserve the void volume provided by the diaper even after insult, thus improving the containment characteristics of the diaper 20. In particular, the second zone 58 may desirably include those areas of the top surface 32 that are in the front waist section 22 and the rear waist section 24 such that advantageous stretch characteristics may be maintained in the waist sections 22 and 24 for improved fit and comfort.

The first and second zone 44 and 58 of the different aspects of the present invention may be provided in the top surface 32 in any number of ways that are well known in the art. Specifically, the top surface 32 may consist of a single layer of fabric such as a stretchable bodyside liner 33. The first zone 44 may be provided in the stretchable bodyside liner 33 in any number of means for restricting the stretchability of the bodyside liner 33. For example, the bodyside liner 33 may be configured to have characteristics that allow the top surface 32 to have localized areas of reduced extendability, thereby providing the first zone 44. In a particular aspect, the layer that provides the top surface 32 may be treated with a chemical that provides a localized resistance to stretching, thereby providing the first zone 44. Simultaneously, the remainder of the top surface 32 would remain substantially untreated, thus retaining the stretch properties of the material, and thereby providing the second zone 58. Suitable chemical treatments include applying a coating of starch onto the top surface 32.

Alternatively, the top surface 32 may be provided by a heat treatable material, such as are well known in the art. In particular, a heat settable material such as a polypropylene or polyethylene fabric may be used to provide the top surface 32. Such heat settable fabrics may then be heat treated in localized areas to provide the first zone 44. Desirably, the remainder of the top surface 33 would not be heat treated, thus retaining the stretch properties of the material, and thereby providing the second zone 58 of the top surface 32. The heat settable fabrics may be treated in many ways as are well known in the art. For example, the fabric may be heated in localized areas by passing the material through a microwave oven, a conventional oven, or the like.

In another alternative, a single layer of fabric providing the top surface 32 may include the first zone 44 via localized thermal bonding of the single layer of fabric. The fabric providing the top surface 32 may be thermally bonded in many ways as are known to those skilled in the art. For example, a bodyside liner 33 that is providing the top surface 32 may be passed through an intermittent rotary ultrasonic bonder to bond a localized area thereby creating the characteristics necessary for the first zone 44. Simultaneously, the remainder of the top surface 32 would remain substantially unbonded, thus retaining the stretch properties of the bodyside liner 33, and thereby providing the second zone 58.

In yet another alternative aspect, the stretchable top surface 32 including the first zone 44 may be provided by multiple layers of materials. For example, as representatively illustrated in FIGS. 1–3, 5 and 7, a portion of the top surface 32 may generally be provided by a first layer of material, such as a stretchable bodyside liner 33, and the first zone 44 of the top surface 32 may be provided by an additional layer of material attached to the bodyside liner 33. Accordingly, the remainder of the bodyside liner would provide the second zone 58 of the top surface 32. In a particular aspect, several layers or pieces of material may be used to provide the first zone 44. Alternatively, the entirety of the top surface 32, including the first and second zones 44 and 58 may include several layers of material.

In a particular aspect, the first zone 44 may be provided by a surge management layer 43. For example, as representatively illustrated in FIGS. 1–3, 5 and 7, the first zone 44 is provided by the surge management layer 43 combined with the bodyside liner 33. At the same time, the second zone 58 is provided by the remaining areas of the bodyside liner 33.

Alternatively, other suitable materials may be used to provide the first zone 44. For example, a layer of tissue may be combined with the other layers that provide the top surface 32 to provide the first zone. The tissue may be a nonwoven, spunbond, polypropylene fabric composed of about 2.8–3.2 denier fibers formed into a web having a basis weight of about 20 grams per square meter and a density of about 0.13 grams per cubic centimeter. The fabric may be surface treated with about 0.3 weight percent of a surfactant commercially available from Hodgson Textile Chemicals, Inc. under the trade designation AHCOVEL Base N-62.

In another aspect, a localized layer of adhesive may be incorporated into the top surface 32 to provide the first zone 44. Suitable adhesives are well known in the art, and may include adhesives described herein as suitable for the assembly of the diaper 20. The adhesive may be applied in various suitable patterns and methods. For example, the adhesive may be applied in a swirl pattern, slot coated, melt blown, control coated, and the like, or combinations thereof.

As explained in great detail above, the first zone 44 desirably possesses stretch characteristics that are less than that of the outer cover 30. In particular, the outer cover 30 desirably defines a first level of elongation when subjected to a tensile force of 100 gmf per inch (per 2.54 cm) of width, while the first zone 44 provides a second level elongation when subjected to a tensile force of 100 gmf per inch (per 2.54 cm) of width that is less than the first level of elongation. In another aspect, the first level of elongation may be at least about 10% while the second level of elongation is less than 10%. In yet another aspect, the first level of elongation may be at least about 20% while the second level of elongation is less than 20%. Desirably, the first level of elongation may be at least about 30% while the second level of elongation is less than 30%. Still more desirably, the first level of elongation may be at least about 40% while the second level of elongation is less than 40%. As has been made clear in this disclosure, the top surface 32 and the outer cover 30 may include materials that extend or deform, and then substantially recover to their original size and shape.

Alternatively, the top surface 32 and the outer cover 30 may be provided by materials that are extensible, that is materials that may extend and then provides substantially permanent deformation as described herein. For example, the outer cover 30 desirably defines a first level of deformation when subjected to a tensile force of 100 gmf per inch (per 2.54 cm) of width, while the first zone 44 provides a second level deformation when subjected to a tensile force of 100 gmf per inch (per 2.54 cm) of width that is less than the first level of permanent deformation. In another aspect, the outer cover 30 may provide a substantially permanent deformation of at least about 15% while the first zone 44 provides a substantially permanent deformation that is less than 15%. In yet another aspect, the outer cover 30 may provide a substantially permanent deformation of at least about 20% while the first zone 44 provides a substantially permanent deformation that is less than 20%.

Further, as explained in detail herein, the first zone 44 can desirably be less stretchable than the second zone 58. For example, the second zone 58 may provide certain levels of elongation when subjected to a tensile force of 100 gmf per inch (per 2.54 cm) of width. As such, the elongation of the first zone 44 desirably does not exceed the level of elongation of the second zone when subjected to a tensile force of 100 gmf per inch (per 2.54 cm) of width. Still more particularly, the first zone 44 may provide an elongation of less than 20% when subjected to a tensile force of 100 gmf per inch (per 2.54 cm) of width while the second zone 58 may simultaneously provide an elongation of at least 20% when subjected to a tensile force of 100 gmf per inch (per 2.54 cm) of width.

However, it should also be understood that in the aspects described above, the second zone 58 of the stretchable top surface 32 remains substantially stretchable. That is, the second zone 58 of the stretchable top surface 32 may also provide an elongation of at least about 20 percent, desirably at least about 25 percent and more desirably at least about 30 percent when subjected to a tensile force of 100 gmf per inch (per 2.54 cm) of width of the test sample according to the Material Elongation and Deformation Tensile Test set forth herein for improved performance. In still other aspects, the second zone 58 of the top surface 32 can provide an elongation that is within the range of from about 20 percent to about 200 percent and desirably from about 25 percent to about 150 percent and still more desirably from about 30 percent to about 100 percent when subjected to a tensile force of 100 gmf per inch (per 2.54 cm) of width of the test sample according to the Material Elongation and Deformation Tensile Test set forth herein for improved performance.

In aspects where the top surface 32 is extensible rather than elastic, such as when the top surface is provided in part by an extensible bodyside liner, the second zone 58 of the top surface 32 can provide a substantially permanent deformation. In particular, the second zone 58 may provide a substantially permanent deformation of at least about 10 percent, desirably at least about 20 percent, and more desirably at least about 30 percent when subjected to a tensile force of 100 gmf per inch (per 2.54 cm) of width of the test sample according to the Material Elongation and Deformation Tensile Test set forth herein.

Substantially permanent deformations less than those set forth above for the second zone 58 may not provided the desired permanent deformation for improved fit, fastening and containment discussed herein. In still other aspects, the second zone 58 of the top surface 32 can provide a substantially permanent deformation of from about 10 to about 100 percent and desirably from about 20 to about 80 percent when subjected to the tensile force of 100 gmf per inch (per 2.54 cm) of width of the test sample according to the Material Elongation and Deformation Tensile Test set forth herein.

Further, the second zone 58 of the top surface 32 can desirably provide a substantially permanent deformation when subjected to a tensile force of 100 gmf per inch (per 2.54 cm) of width, while the substantially permanent deformation provided by the first zone 44 is less than that of the second zone 58 when subjected to a tensile force of 100 gmf per inch (per 2.54 cm) of width. In another aspect, the second zone 58 may provide a substantially permanent deformation of at least about 10% while the first zone 44 provides a substantially permanent deformation that is less than 10%. In yet another aspect, the second zone 58 may provide a substantially permanent deformation of at least about 20% while the first zone 44 provides a substantially permanent deformation that is less than 20%.

In general, it is advantageous to have the second zone 58 of the top surface 32 to have similar stretch characteristics to that of the outer cover 30. As such, the top surface 32 will not substantially restrict the stretch capabilities of the outer cover 30, and similarly, the outer cover 30 will not substantially restrict the stretch capabilities of the top surface 32. In such an arrangement, the diaper 20 is configured to provide improved fit and containment in use for the wearer. It should be noted, however, that the outer cover 30 may be made less stretchable with the attachment of various non-stretchable components. As such, the advantage of restricting the stretchability of the top surface 32 in the first zone 44 to improve containment and maintain void volume becomes more evident.

The different aspects of the present invention advantageously provide absorbent articles that have a stretchable outer cover that provides improved fit and improved resistance to leakage. In particular, the stretchable outer cover is capable of adjusting to the wearer's movements and changes in body dimensions for improved performance. In addition, the stretchable outer cover on the articles provides improved breathability, greater softness, and more cloth-like properties. Moreover, in certain aspects, the present invention can also advantageously provide pant-like, prefastened, absorbent articles that are capable of being reliably pulled up or down over the hips of the wearer to assist in the toilet training of the wearer similar to conventional training pants.

Test Procedures

Material Elongation and Deformation Tensile Test

A suitable technique for determining the amount of elongation, retractive force and or permanent deformation of a selected component or material can employ ASTM Standard Test Method D882 (Tensile Method for Tensile Properties of Thin Plastic Sheeting) dated December 1995, with the following particulars.

Equipment

1. Tensile tester capable of obtaining a peak load and equipped with an appropriate load cell. A suitable tensile testing system is a Sintech Tensile Tester, commercially available from MTS Sintech, Research Triangle Park, N.C., under the trade designation Model 1/G equipped with Sintech Testworks™ Version 3.10 Software.
2. Pneumatic-action grips having a 0.5 by 4 inch grip face.
3. Test facility having a temperature of 23±1° C., and a relative humidity of 50±2 percent.

The test sample width is perpendicular to the direction of the tensile force applied during the testing. With regard to the shown configurations, for example, the test sample "width" generally corresponds to the length-wise dimension of outer cover 30 along the longitudinal direction 48 of the article. The initial separation of the jaws of the tensile tester is 3 inches (76.2 mm) at a tensile force of about 1 gram force per inch of width of the test sample, and the moving jaw is moved at a constant rate of 127 mm/min. The moving jaw is stopped at an extension where the tensile force equals 100 grams force per inch of width of the test sample, held at that extension for a period of 2 minutes, and then returned back to its initial tensile force of about 1 gram force per inch of width of the test sample at a rate of 127 mm/min.

The percentage of elongation, extension or permanent deformation can be determined in accordance with the following formula:

$$100*(L-L_O)/(L_O);$$

where: L=either a) extended length for elongation or extension or b) post extended length for set or deformation, and $L_O$=initial length.

EXAMPLES

The following examples are presented to provide a more detailed understanding of the invention. The examples are representative, and are not intended to limit the scope of the invention.

Example 1

Absorbent Articles were prepared in accordance with the present invention. Specifically, as representatively illustrated in FIG. 9, necked laminates suitable for the stretchable outer cover 30 of the present invention were adhered to an extensible fabric suitable for the stretchable top surface 32 of the present invention. The outer cover 30 consisted of unnecked 8556 PLIANT FILM and a 45% necked 0.4 osy polypropylene spunbond outercover adhered to each other using National Starch adhesive at an add on rate of 4 gsm. The top surface 32 consisted of a 35% necked 0.4 osy polypropylene spunbond nonwoven. The outer cover and the top surface were adhered together with #922XL two sided tape 74 available from 3M. An absorbent body 34 was sandwiched between the top surface 32 and the outer cover 30 and consisted of a 3900 GSM mix of 60% Alliance CR1654 bleached softwood pulp fiber and 40% FAVOR SXM 9543 superabsorbent polymer. In addition the top surface included a surge management layer 43 to provide the first zone 44. The surge management layer was a 3 osy high capacity surge. These articles are described herein as code 1.

Likewise, similar absorbent articles were prepared in the same way, only the surge management layer 43 was omitted, and thus, the articles did not have a first zone 44. These articles are described herein as code 2.

Five samples of each code were prepared. As representatively illustrated in FIG. 9, the top surface curvilinear cross sectional distance 70 of the article was marked and measured in the lateral direction 50 prior to testing. Similarly, the outer cover curvilinear cross sectional distance 72 of the article is marked and measured in the lateral direction 50 prior to testing.

Measuring the curvilinear cross sectional distances 70 and 72 may be completed by extending a flexible fabric measuring tape or ruler directly along the curvilinear cross sectional distances 70 and 72. Alternatively, a rigid measuring device such as a ruler may be gently rolled along the curvilinear cross sectional distances 70 and 72 to obtain the necessary measurement.

Figure 8:
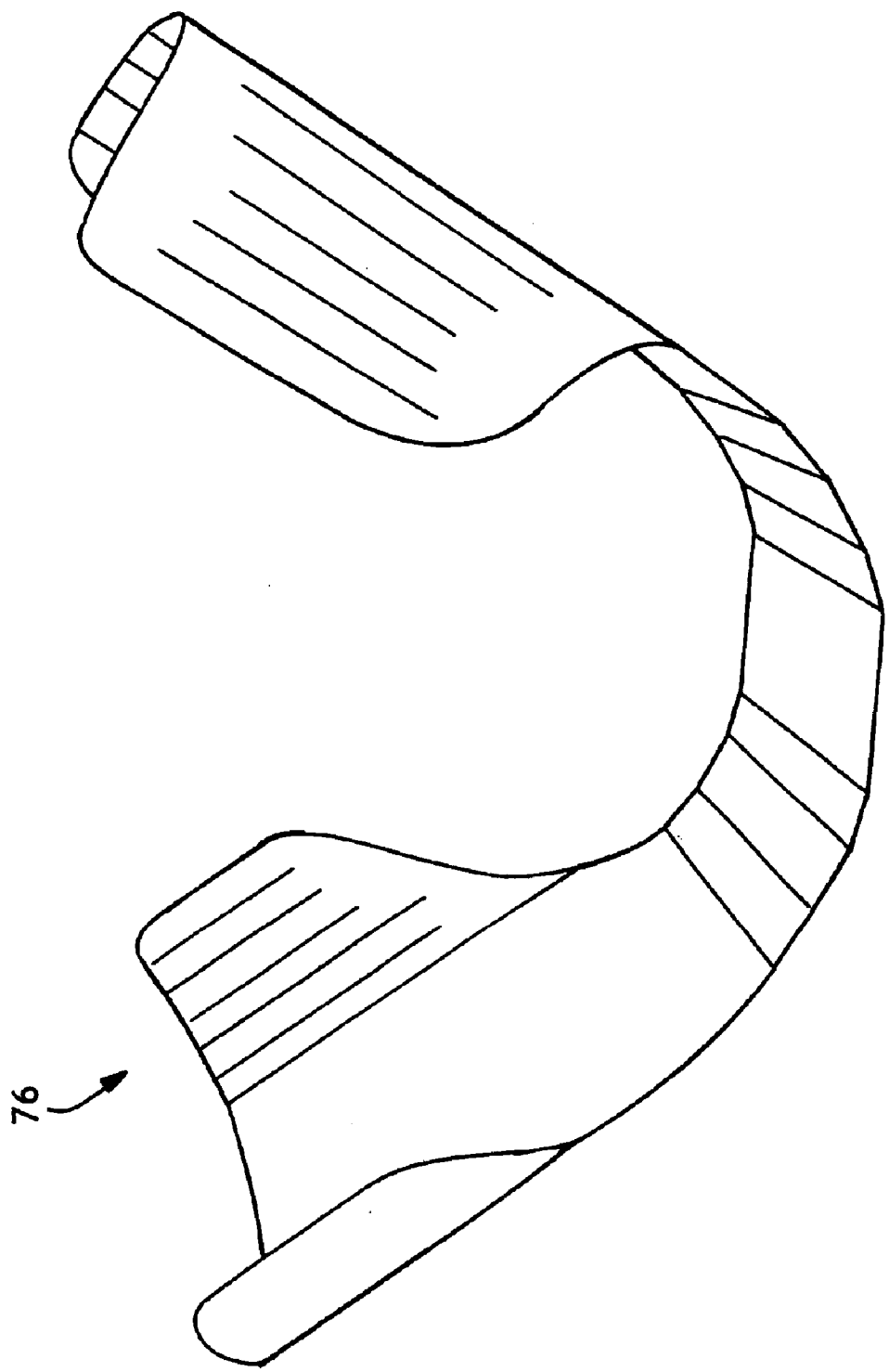
FIG. 8 representatively shows a plan view of a cradle suitable for use in connection with the Example described herein.

The samples were placed into a cradle 76 to prevent fluid run-off as fluid is added. A suitable cradle 76 is representatively illustrated in FIG. 8. As mentioned above, the cradle 76 allows for the addition of fluid to the absorbent article without any of the fluid running out of the article. Thus the cradle ensures that an accurate amount of fluid may be added to each sample. The cradle may be made of any suitable material as is well known to those skilled in the art. For example, the cradle may be made or plexiglass or plastic.

600 ml of tap water was added to each of the absorbent articles of each code. The articles were removed from the cradle 76 once all the fluid was absorbed into the article.

The top surface curvilinear cross sectional distance 70 of the article was once again measured in the lateral direction 50. Similarly, the outer cover curvilinear cross sectional distance 72 of the article was again measured in the lateral direction 50. Suitable measuring methods are described above. The results are set forth in Table 1 below.

TABLE 1

| SAMPLE | Absorbent Weight (g) | Top Surface Curvilinear Cross sectional Distance Before (mm) | Top Surface Curvilinear Cross sectional Distance After (mm) | Top Surface Curvinear Cross sectional Distance Difference (mm) | Outer Cover Curvilinear Cross sectional Distance Before (mm) | Outer Cover Curvilinear Cross sectional Distance After (mm) | Outer Cover Curvilinear Cross sectional Distance Difference (mm) |
|---|---|---|---|---|---|---|---|
| CODE 1 - Samples with a first zone | | | | | | | |
| 1 | 26.3 | 104 | 116 | 12 | 104 | 134 | 30 |
| 2 | 26.6 | 105 | 119 | 14 | 107 | 130 | 23 |
| 3 | 25.9 | 108 | 120 | 12 | 106 | 131 | 25 |
| 4 | 27.0 | 105 | 116 | 11 | 104 | 134 | 30 |

TABLE 1-continued

| SAMPLE | Absorbent Weight (g) | Top Surface Curvilinear Cross sectional Distance Before (mm) | Top Surface Curvilinear Cross sectional Distance After (mm) | Top Surface Curvinear Cross sectional Distance Difference (mm) | Outer Cover Curvilinear Cross sectional Distance Before (mm) | Outer Cover Curvilinear Cross sectional Distance After (mm) | Outer Cover Curvilinear Cross sectional Distance Difference (mm) |
|---|---|---|---|---|---|---|---|
| 5 | 26.4 | 104 | 115 | 11 | 105 | 134 | 29 |
| Average | | 105 | 117 | 12 | 105 | 132 | 27 |
| CODE 2 - Samples without a first zone | | | | | | | |
| 1 | 26.0 | 105 | 156 | 51 | 102 | 120 | 18 |
| 2 | 25.2 | 104 | 149 | 45 | 105 | 120 | 15 |
| 3 | 23.6 | 102 | 138 | 36 | 105 | 125 | 20 |
| 4 | 24.0 | 101 | 152 | 51 | 103 | 120 | 17 |
| 5 | 24.0 | 98 | 150 | 52 | 102 | 117 | 15 |
| Average | | 102 | 149 | 47 | 103 | 120 | 17 |

The results show that upon insult the Code 1 samples extended the outer cover more than the top surface while the Code 2 samples extended the top surface more than the outer cover. Accordingly, the Code 1 sample, which included a first zone, would better preserve the void volume that may be provided in an absorbent article of the present invention. That is, the expansion of the absorbent body upon insult expanded and deformed the stretchable top surface in Code 1 an average of 12 mm, while the expansion of the absorbent body in Code 2 expanded and deformed the top surface an average of 47 mm. As such, the absorbent body of code 2, without the benefit of a first zone in the top surface would be more likely to consume any void volume that may be created by other components that may be included with an absorbent article, such as a pair of containment flaps. In such a situation, bodily exudates contained within the void volume would be able to pass over the top of the containment flaps because of the expansion of the absorbent body being able to displace the stretchable top surface. In addition, the expansion of the absorbent body into the void volume of the diaper may push the rest of the diaper away from the wearer. Therefore, components such as leg and waist elastics may no longer be able to have close contact with the wearer, which in turn may undesirably result in unsatisfactory fit and containment performance of the diaper.

Conversely, in the article of Code 1, containing a first zone, the void volume provided by the diaper would be better maintained. That is, with the expansion of the absorbent body upon insult, the outer cover of the absorbent article of Code 1 expanded more than the top surface. Specifically, the outer cover extended an average of 27 mm while the top surface only extended an average of 12 mm. Moreover, the outer cover of Code 2 extended only an average of 17 mm. The above indicates that the first zone included in the top surface of Code 1 caused the outer cover to expand more than in an absorbent article without a first zone. As such, void volume is better maintained, thereby improving the containment characteristics of the article and reducing the possibility of leakage.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. A disposable absorbent article which defines a front waist section, a rear waist section, an intermediate section which extends between and connects said waist sections, a pair of laterally opposed side edges, a pair of longitudinally opposed waist edges, a longitudinal direction and a lateral direction, said absorbent article comprising:
   a) a substantially liquid-impermeable stretchable outer cover configured to provide a first level of elongation;
   b) a liquid permeable stretchable top surface attached to said stretchable outer cover; said stretchable top surface having a first zone that is configured to provide a second level of elongation that is less than said first level of elongation, said first zone of said top surface is provided by a stretchable bodyside liner and a means for restricting the stretchability of said stretchable bodyside liner;
   c) at least one containment component attached to said liquid permeable top surface; and
   d) an absorbent body located between said stretchable outer cover and said stretchable top surface.

2. The disposable absorbent article of claim 1 wherein said top surface is an extensible bodyside liner.

3. The disposable absorbent article of claim 2 wherein said extensible bodyside liner is a necked nonwoven.

4. The disposable absorbent article of claim 1 wherein said first zone is provided by a combination of a surge layer attached to said extensible bodyside liner.

5. The disposable absorbent article of claim 1 wherein said first zone is provided by a combination of a tissue layer attached to said extensible bodyside liner.

6. The disposable absorbent article of claim 1 wherein said first zone is provided by a combination of a layer of adhesive applied to said extensible bodyside liner.

7. The disposable absorbent article of claim 6 wherein said layer of adhesive is in a swirl pattern.

8. The disposable absorbent article of claim 1 wherein said first zone is provided by a heat settable bodyside liner.

9. The disposable absorbent article of claim 1 wherein said stretchable outer cover comprises a necked laminate which includes at least one layer of a non-elastic neckable material and at least one layer of a non-elastic film.

10. The disposable absorbent article of claim 1 wherein said first zone at least partially overlaps said absorbent body.

11. The disposable absorbent article of claim 1 wherein said first level of elongation is at least about 20 percent and said second level of elongation is less than 20 percent when subjected to said tensile force of 100 gmf per inch (per 2.54 cm) of width.

12. The disposable absorbent article of claim 1 wherein said first level of elongation is at least about 40 percent and said second level of elongation is less than 40 percent when subjected to said tensile force of 100 gmf per inch (per 2.54 cm) of width.

13. The disposable absorbent article of claim 1 wherein said top surface further defines a second zone and wherein said second level of elongation does not exceed a level of elongation provided by said second zone of the top surface.

14. The disposable absorbent article of claim 13 wherein said stretchable outer cover is further configured to provide a substantially permanent deformation of at least about 20 percent when subjected to said tensile force of 100 gmf per inch (per 2.54 cm) of width;

said first zone of said stretchable top surface is further configured to provide a substantially permanent deformation of less than 20 percent when subjected to said tensile force of 100 gmf per inch (per 2.54 cm) of width; and said second zone of said stretchable top surface is further configured to provide a substantially permanent deformation of at least about 20 percent when subjected to said tensile, force of 100 gmf per inch (per 2.54 cm) of width.

15. The disposable absorbent article of claim 1 wherein upon swelling of said absorbent body said absorbent body elongates said stretchable outer cover more than said stretchable top surface.

16. A pant-like, prefastened, disposable absorbent article which defines a front waist section, a rear waist section, an intermediate section which extends between and connects said waist sections, a pair of laterally opposed side edges, a pair of longitudinally opposed waist edges, a longitudinal direction and a lateral direction, said pant-like absorbent article comprising:
   a) a substantially liquid-impermeable stretchable outer cover configured to provide a first level of elongation;
   b) a liquid permeable stretchable top surface attached to said stretchable outer cover; said top surface having a first zone that is configured to provide a second level of elongation that is less than said first level of elongation said first zone of said top surface is provided by a stretchable bodyside liner and a means for restricting the stretchability of said stretchable bodyside liner;
   c) at least one containment component attached to said liquid permeable top surface;
   d) an absorbent body located between said stretchable outer cover and said stretchable top surface; and
   e) a pair of fasteners refastenably attaching said laterally opposed side edges in said front waist section to said laterally opposed side edges in said rear waist section to provide said pant-like, prefastened absorbent article prior to packaging.

17. The pant-like, prefastened disposable absorbent article of claim 16 wherein said top surface is an extensible bodyside liner.

18. The pant-like, prefastened disposable absorbent article of claim 17 wherein said extensible bodyside liner is a necked nonwoven.

19. The pant-like, prefastened disposable absorbent article of claim 16 wherein said first zone is provided by a combination of a surge layer attached to said extensible bodyside liner.

20. The pant-like, prefastened disposable absorbent article of claim 16 wherein said first zone is provided by a combination of a tissue layer attached to said extensible bodyside liner.

21. The pant-like, prefastened disposable absorbent article of claim 16 wherein said first zone is provided by a combination of a layer of adhesive applied to said extensible bodyside liner.

22. The pain-like, prefastened disposable absorbent article of claim 21 wherein said layer of adhesive is in a swirl pattern.

23. The pant-like, prefastened disposable absorbent article of claim 16 wherein said first zone is provided by a heat settable bodyside liner.

24. The pant-like, prefastened disposable absorbent article of claim 16 wherein said stretchable outer cover comprises a necked laminate which includes at least one layer of a non-elastic neckable material and at least one layer of a non-elastic film.

25. The pant-like, prefastened disposable absorbent article of claim 16 wherein said first zone at least partially overlaps said absorbent body.

26. The pant-like, prefastened disposable absorbent article of claim 16 wherein said first level of elongation is at least about 20 percent and said second level of elongation is less than 20 percent when subjected to a tensile force of 100 gmf per inch (per 2.54 cm) of width according to said Material Elongation and Deformation Tensile Test.

27. The pant-like, prefastened disposable absorbent article of claim 16 wherein said first level of elongation is at least about 40 percent and said second level of elongation is less than 40 percent when subjected to a tensile force of 100 gmf per inch (per 2.54 cm) of width according to said Material Elongation and Deformation Tensile Test.

28. The pant-like, prefastened disposable absorbent article of claim 16 wherein said top surface further defines a second zone, and wherein said second level of elongation does not exceed a level of elongation provided by said second zone of said top surface.

29. The pant-like, prefastened disposable absorbent article of claim 28 wherein said stretchable outer cover is further configured to provide a substantially permanent deformation of at least about 20 percent when subjected to said tensile force of 100 gmf per inch (per 2.54 cm) of width;

said first zone of said stretchable top surface is further configured to provide a substantially permanent deformation of less than 20 percent when subjected to said tensile force of 100 gmf per inch (per 2.54 cm) of width; and said second zone of said stretchable top surface is further configured to provide a substantially permanent deformation of at least about 20 percent when subjected to said tensile force of 100 gmf per inch (per 2.54 cm) of width.

30. The pant-like, prefastened disposable absorbent article of claim 16 wherein upon swelling of said absorbent body said absorbent body elongates said stretchable outer cover more than said stretchable top surface.

31. A disposable absorbent article which defines a front waist section, a rear waist section, an intermediate section which extends between and connects said waist sections, a pair of laterally opposed side edges, a pair of longitudinally opposed waist edges, a longitudinal direction and a lateral direction, said absorbent article comprising:
   a) a substantially liquid-impermeable stretchable outer cover configured to provide a first level of elongation;
   b) a liquid permeable stretchable bodyside liner attached to said stretchable outer cover;
   c) a pair of containment flaps attached to said liquid permeable stretchable bodyside liner;

d) a surge layer attached to said liquid permeable stretchable bodyside liner; and e) an absorbent body located between said stretchable outer cover and said stretchable bodyside liner;

wherein said stretchable bodyside liner and said surge layer combine to provide a first zone that is configured to provide a second level of elongation that is less than the first level of elongation.

32. The disposable absorbent article of claim 31 wherein said extensible bodyside liner is a necked nonwoven.

33. The disposable absorbent article of claim 32 said stretchable outer cover comprises a necked laminate which includes at least one layer of a non-elastic neckable material and at least one layer of non-elastic film.

34. The disposable absorbent article of claim 32 wherein said first zone at least partially overlaps said absorbent body.

35. The disposable absorbent article of claim 32 wherein said first level of elongation is at least about 20 percent and said second level of elongation is less than 20 percent when subjected to a tensile force of 100 gmf per inch (per 2.54 cm) of width according to said Material Elongation and Deformation Tensile Teat.

36. The disposable absorbent article of claim 32 wherein said first level of elongation is at least 40 percent and said second level of elongation is less than 40 percent when subjected to a tensile force of 100 gmf per inch (per 2.54 cm) of width according to said Material Elongation and Deformation Tensile Test.

37. The disposable absorbent article of claim 32 wherein said bodyside liner alone provides a second zone and said second level of elongation does not exceed a level of elongation provided by said second zone of said top surface.

38. The disposable absorbent article of claim 32 wherein said stretchable outer cover is further configured to provide a substantially permanent deformation of at least about 20 percent when subjected to said tensile force of 100 gmf per inch (per 2.54 cm) of width;

said first zone of said extensible bodyside liner is further configured to provide a substantially permanent deformation of less than 20 percent when subjected to said tensile force of 100 gmf per inch (per 2.54 cm) of width; and said second zone of said extensible bodyside liner is further configured to provide a substantially permanent deformation of at least about 20 percent when subjected to said tensile force of 100 gmf per inch (per 2.54 cm) of width.

39. The disposable absorbent article of claim 31 wherein upon swelling of said absorbent body said absorbent body elongates said stretchable outer cover more than said stretchable bodyside liner.

40. A disposable absorbent article which defines a front waist section, a rear waist section, an intermediate section which extends between and connects said waist sections, a pair of laterally opposed side edges, a pair of longitudinally opposed waist edges, a longitudinal direction and a lateral direction, said absorbent article comprising:

a) a substantially liquid-impermeable stretchable outer cover;

b) a liquid permeable stretchable top surface attached to said stretchable outer cover; said stretchable top surface having a first zone and a second zone wherein said second zone provides an elongation that is at least about 20 percent and said first zone provides an elongation that is less than 20 percent when subjected to a tensile force of 100 gmf per inch (per 2.54 cm) of width;

c) at least one containment component attached to said liquid permeable top surface; and d) an absorbent body located between said stretchable outer cover and said stretchable top surface.

41. The disposable absorbent article of claim 40 wherein said top surface is an extensible bodyside liner.

42. The disposable absorbent article of claim 41 wherein said extensible bodyside liner is a necked nonwoven.

43. The disposable absorbent article of claim 40 wherein said first zone is provided by a combination of a surge layer attached to an extensible bodyside liner.

44. The disposable absorbent article of claim 40 wherein said first zone at least partially overlaps said absorbent body.

* * * * *

UNITED STATES PATENT AND TRADEMARK OFFICE
CERTIFICATE OF CORRECTION

PATENT NO. : 6,840,928 B2
DATED : January 11, 2005
INVENTOR(S) : Paul J. Datta et al.

It is certified that error appears in the above-identified patent and that said Letters Patent is hereby corrected as shown below:

Column 33,
Line 11, delete "32" and substitute -- 31 wherein --
Lines 15, 17, 23, 29 and 33, delete "32" and substitute -- 31 --

Signed and Sealed this

Seventeenth Day of May, 2005

JON W. DUDAS
*Director of the United States Patent and Trademark Office*